(12) United States Patent
Frey et al.

(10) Patent No.: US 12,357,413 B2
(45) Date of Patent: *Jul. 15, 2025

(54) PATIENT-MATCHED APPARATUS FOR USE IN SPINE RELATED SURGICAL PROCEDURES AND METHODS FOR USING THE SAME

(71) Applicant: Mighty Oak Medical, Inc., Englewood, CO (US)

(72) Inventors: George Frey, Englewood, CO (US); Caleb Voelkel, Lakewood, CO (US); Adam Jensen, Golden, CO (US)

(73) Assignee: Mighty Oak Medical, Inc., Englewood, CO (US)

( * ) Notice: Subject to any disclaimer, the term of this patent is extended or adjusted under 35 U.S.C. 154(b) by 51 days.

This patent is subject to a terminal disclaimer.

(21) Appl. No.: 18/502,667

(22) Filed: Nov. 6, 2023

(65) Prior Publication Data

US 2024/0065800 A1 Feb. 29, 2024

Related U.S. Application Data

(63) Continuation of application No. 17/402,512, filed on Aug. 14, 2021, now Pat. No. 11,806,197, which is a
(Continued)

(51) Int. Cl.
*A61B 90/00* (2016.01)
*A61B 17/70* (2006.01)
(Continued)

(52) U.S. Cl.
CPC .......... *A61B 90/36* (2016.02); *A61B 17/7001* (2013.01); *A61B 17/7047* (2013.01);
(Continued)

(58) Field of Classification Search
CPC . A61B 90/36; A61B 17/7001; A61B 17/7047; A61B 17/7083; A61B 17/88;
(Continued)

(56) References Cited

U.S. PATENT DOCUMENTS

| 3,151,392 A | 10/1964 | Chambers |
| 5,098,383 A | 3/1992 | Hemmy et al. |

(Continued)

FOREIGN PATENT DOCUMENTS

| CA | 2736525 | 3/2010 |
| CA | 2862341 | 8/2013 |

(Continued)

OTHER PUBLICATIONS

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
(Continued)

*Primary Examiner* — Sanjay Cattungal
(74) *Attorney, Agent, or Firm* — FisherBroyles, LLP; Ian R. Walsworth

(57) ABSTRACT

The present disclosure relates to embodiments of a patient-specific or patient-matched, customized apparatus for assisting in various surgical procedures. In varying embodiments, patient-specific guides may comprise multiple patient-specific surfaces for mating with the underlying patient anatomy and may further comprise one or more protrusions or projections for facilitating placement and attachment, at least temporarily, to the desired location of the patient's anatomy. The apparatus described herein are preferably used with cervical and/or certain thoracic levels of the human
(Continued)

spine and may comprise single or multi-level guides for placement of instruments and/or implants during a variety of surgical procedures.

15 Claims, 34 Drawing Sheets

Related U.S. Application Data continuation of application No. 16/831,215, filed on Mar. 26, 2020, now Pat. No. 11,633,254, which is a continuation-in-part of application No. 16/598,861, filed on Oct. 10, 2019, now Pat. No. 11,376,073, which is a continuation-in-part of application No. 15/997,404, filed on Jun. 4, 2018, now Pat. No. 11,039,889, which is a continuation-in-part of application No. 15/416,975, filed on Jan. 26, 2017, now Pat. No. 9,987,024, which is a continuation-in-part of application No. 14/883,299, filed on Oct. 14, 2015, now Pat. No. 9,642,633, which is a continuation-in-part of application No. 14/298,634, filed on Jun. 6, 2014, now Pat. No. 9,198,678, which is a continuation-in-part of application No. 13/841,069, filed on Mar. 15, 2013, now Pat. No. 8,870,889, which is a continuation-in-part of application No. 13/172,683, filed on Jun. 29, 2011, now Pat. No. 8,758,357.

(60) Provisional application No. 62/823,911, filed on Mar. 26, 2019, provisional application No. 62/743,661, filed on Oct. 10, 2018, provisional application No. 62/628,626, filed on Feb. 9, 2018, provisional application No. 62/162,466, filed on May 15, 2015, provisional application No. 61/877,837, filed on Sep. 13, 2013, provisional application No. 61/845,463, filed on Jul. 12, 2013, provisional application No. 61/832,583, filed on Jun. 7, 2013, provisional application No. 61/625,559, filed on Apr. 17, 2012, provisional application No. 61/393,695, filed on Oct. 15, 2010, provisional application No. 61/359,710, filed on Jun. 29, 2010.

(51) Int. Cl.
*A61B 17/88* (2006.01)
*A61B 34/10* (2016.01)
*A61B 17/00* (2006.01)
*A61B 17/56* (2006.01)
*A61B 17/90* (2006.01)
*A61B 34/00* (2016.01)
*A61B 34/20* (2016.01)
*A61B 90/50* (2016.01)

(52) U.S. Cl.
CPC .......... *A61B 17/7083* (2013.01); *A61B 17/88* (2013.01); *A61B 34/10* (2016.02); *A61B 2017/00203* (2013.01); *A61B 2017/568* (2013.01); *A61B 17/90* (2021.08); *A61B 2034/102* (2016.02); *A61B 2034/107* (2016.02); *A61B 2034/108* (2016.02); *A61B 2034/2048* (2016.02); *A61B 34/76* (2016.02); *A61B 2090/0807* (2016.02); *A61B 2090/365* (2016.02); *A61B 2090/372* (2016.02); *A61B 2090/3916* (2016.02); *A61B 2090/3975* (2016.02); *A61B 2090/3983* (2016.02); *A61B 2090/3987* (2016.02); *A61B 2090/3995* (2016.02); *A61B 2090/502* (2016.02)

(58) Field of Classification Search
CPC ......... A61B 34/10; A61B 17/90; A61B 34/76; A61B 2017/00203; A61B 2017/568; A61B 2034/102; A61B 2034/107; A61B 2034/108; A61B 2034/2048; A61B 2090/0807; A61B 2090/365; A61B 2090/372; A61B 2090/3916; A61B 2090/3975; A61B 2090/3983; A61B 2090/3987; A61B 2090/3995; A61B 2090/502; A61B 2017/00526; A61B 34/20; A61B 2017/1602; A61B 2034/105; A61B 2090/033; A61B 17/1757; A61B 17/7067; A61B 17/7071; A61B 90/11; A61B 17/1671
See application file for complete search history.

(56) References Cited

U.S. PATENT DOCUMENTS

| | | |
|---|---|---|
| 5,201,734 A | 4/1993 | Cozad et al. |
| D359,557 S | 6/1995 | Hayes |
| 5,490,409 A | 2/1996 | Weber |
| 5,527,312 A | 6/1996 | Ray |
| 5,569,246 A | 10/1996 | Ojima et al. |
| 5,733,284 A | 3/1998 | Martin |
| D403,066 S | 12/1998 | DeFonzo |
| 5,865,846 A | 2/1999 | Bryan et al. |
| D412,032 S | 7/1999 | Mikula-Curtis et al. |
| 5,993,453 A | 11/1999 | Bullara et al. |
| 6,006,581 A | 12/1999 | Holmes |
| D420,132 S | 2/2000 | Bucholz et al. |
| 6,030,401 A | 2/2000 | Marino |
| 6,035,691 A | 3/2000 | Lin et al. |
| 6,063,088 A | 5/2000 | Winslow |
| D428,989 S | 8/2000 | Segermark et al. |
| 6,113,602 A | 9/2000 | Sand |
| 6,142,998 A | 11/2000 | Smith et al. |
| 6,221,077 B1 | 4/2001 | Rinner et al. |
| 6,290,724 B1 | 9/2001 | Marino |
| 6,309,395 B1 | 10/2001 | Smith et al. |
| 6,328,738 B1 | 12/2001 | Suddaby |
| 6,342,056 B1 | 1/2002 | Mac-Thiong |
| 6,364,880 B1 | 4/2002 | Michelson |
| 6,644,087 B1 | 11/2003 | Ralph et al. |
| 6,711,432 B1 | 3/2004 | Krause |
| 6,719,795 B1 | 4/2004 | Cornwall |
| 6,755,839 B2 | 6/2004 | Van Hoeck et al. |
| 7,014,640 B2 | 3/2006 | Kemppanien et al. |
| 7,025,769 B1 | 4/2006 | Ferree |
| 7,077,864 B2 | 7/2006 | Byrd, III et al. |
| D532,515 S | 11/2006 | Buttler et al. |
| D533,664 S | 12/2006 | Buttler et al. |
| 7,207,992 B2 | 4/2007 | Ritland |
| 7,235,076 B2 | 6/2007 | Pacheco |
| 7,288,093 B2 | 10/2007 | Michelson |
| 7,341,590 B2 | 3/2008 | Ferree |
| 7,387,643 B2 | 6/2008 | Michelson |
| 7,406,775 B2 | 8/2008 | Funk et al. |
| 7,454,939 B2 | 11/2008 | Garner et al. |
| 7,491,180 B2 | 2/2009 | Pacheco |
| 7,559,931 B2 | 7/2009 | Stone |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,955,355 B2 | 6/2011 | Cin |
| 7,957,824 B2 | 6/2011 | Boronvinskih et al. |
| 7,957,831 B2 | 6/2011 | Isaacs |
| 7,967,868 B2 | 6/2011 | White et al. |
| D642,263 S | 7/2011 | Park |
| D649,245 S | 11/2011 | Klebs |
| 8,057,482 B2 | 11/2011 | Stone et al. |
| 8,070,752 B2 | 12/2011 | Metzger et al. |
| 8,092,465 B2 | 1/2012 | Metzger et al. |

(56) References Cited

U.S. PATENT DOCUMENTS

| | | |
|---|---|---|
| 8,118,815 B2 | 2/2012 | van der Walt |
| 8,159,753 B2 | 4/2012 | Ojeda et al. |
| 8,167,884 B2 | 5/2012 | Pacheco |
| 8,175,683 B2 | 5/2012 | Roose |
| 8,206,396 B2 | 6/2012 | Trabish |
| 8,214,014 B2 | 7/2012 | Pacheco |
| 8,236,006 B2 | 8/2012 | Hamada |
| 8,241,293 B2 | 8/2012 | Stone |
| 8,257,083 B2 | 9/2012 | Berckmans |
| D669,176 S | 10/2012 | Frey |
| D669,984 S | 10/2012 | Cheney et al. |
| 8,277,461 B2 | 10/2012 | Pacheco |
| 8,282,646 B2 | 10/2012 | Schoenefeld |
| 8,298,235 B2 | 10/2012 | Grinberg |
| 8,298,237 B2 | 10/2012 | Schoenefeld |
| 8,298,242 B2 | 10/2012 | Justis et al. |
| D672,038 S | 12/2012 | Frey |
| 8,357,111 B2 | 1/2013 | Caillouette et al. |
| 8,377,066 B2 | 2/2013 | Katrana et al. |
| 8,407,067 B2 | 3/2013 | Ulthgenannt et al. |
| 8,419,740 B2 | 4/2013 | Aram et al. |
| D685,087 S | 6/2013 | Voic |
| 8,460,303 B2 | 6/2013 | Park |
| 8,480,679 B2 | 7/2013 | Park et al. |
| 8,535,387 B2 | 9/2013 | Meridew et al. |
| 8,540,719 B2 | 9/2013 | Peukert et al. |
| D691,719 S | 10/2013 | Park |
| 8,545,509 B2 | 10/2013 | Park et al. |
| 8,549,888 B2 | 10/2013 | Isaacs |
| 8,568,487 B2 | 10/2013 | Witt et al. |
| 8,591,516 B2 | 11/2013 | Metzger et al. |
| 8,603,180 B2 | 12/2013 | White et al. |
| 8,607,603 B2 | 12/2013 | Justis et al. |
| 8,608,748 B2 | 12/2013 | Metzger et al. |
| 8,608,749 B2 | 12/2013 | Witt et al. |
| 8,632,547 B2 | 1/2014 | Metzger et al. |
| 8,668,700 B2 | 3/2014 | Catanzarite |
| D705,929 S | 5/2014 | Frey |
| 8,721,651 B2 | 5/2014 | Loke et al. |
| 8,758,357 B2 | 6/2014 | Frey |
| 8,808,302 B2 | 8/2014 | White et al. |
| 8,808,303 B2 | 8/2014 | Stemniski et al. |
| 8,858,561 B2 | 10/2014 | White et al. |
| 8,864,769 B2 | 10/2014 | Stone et al. |
| 8,870,889 B2 | 10/2014 | Frey |
| D718,862 S | 12/2014 | Matheny |
| D718,863 S | 12/2014 | Matheny |
| D718,864 S | 12/2014 | Matheny |
| 8,979,749 B2 | 3/2015 | Gorek et al. |
| 8,992,538 B2 | 3/2015 | Keefer |
| D726,914 S | 4/2015 | Matheny |
| 9,017,412 B2 | 4/2015 | Wolters et al. |
| 9,044,285 B2 | 6/2015 | Harper |
| 9,066,727 B2 | 6/2015 | Catanzarite et al. |
| 9,066,816 B2 | 6/2015 | Allard et al. |
| 9,113,971 B2 | 8/2015 | Metzger et al. |
| D738,498 S | 9/2015 | Frey et al. |
| 9,138,325 B2 | 9/2015 | Mouw |
| 9,173,661 B2 | 11/2015 | Metzger et al. |
| 9,192,446 B2 | 11/2015 | Piferi |
| D745,671 S | 12/2015 | Frey et al. |
| D745,672 S | 12/2015 | Frey et al. |
| D745,673 S | 12/2015 | Frey et al. |
| 9,198,678 B2 | 12/2015 | Frey |
| D747,480 S | 1/2016 | Geebelen |
| D747,481 S | 1/2016 | Geebelen |
| 9,289,253 B2 | 3/2016 | Sweeney |
| 9,451,973 B2 | 9/2016 | Heilman |
| 9,486,324 B2 | 11/2016 | Hochschuler |
| D775,335 S | 12/2016 | Frey et al. |
| 9,642,633 B2 | 5/2017 | Frey et al. |
| 9,649,160 B2 | 5/2017 | van der Walt et al. |
| 9,662,157 B2 | 5/2017 | Schneider et al. |
| 9,675,400 B2 | 6/2017 | Katrana et al. |
| 9,737,339 B2 | 8/2017 | Copp et al. |
| 9,814,497 B1 | 11/2017 | Al-Habib et al. |
| 9,826,991 B2 | 11/2017 | Kaiser et al. |
| 9,839,448 B2 | 12/2017 | Reckling et al. |
| 9,848,922 B2 | 12/2017 | Tohmeh et al. |
| 9,913,669 B1 | 3/2018 | Scholl et al. |
| 9,949,843 B2 | 4/2018 | Reiley et al. |
| 9,968,408 B1 | 5/2018 | Casey et al. |
| 9,987,024 B2 | 6/2018 | Frey et al. |
| 10,085,784 B2 | 10/2018 | Ono et al. |
| 10,166,033 B2 | 1/2019 | Keiley et al. |
| D857,893 S | 8/2019 | Frey |
| D858,765 S | 9/2019 | Frey |
| D895,111 S | 9/2020 | Frey |
| 11,039,889 B2 | 6/2021 | Frey |
| 2004/0097925 A1 | 5/2004 | Boehm et al. |
| 2004/0144149 A1 | 7/2004 | Strippgen et al. |
| 2004/0243481 A1 | 12/2004 | Bradbury et al. |
| 2005/0148843 A1 | 7/2005 | Roose |
| 2005/0177156 A1 | 8/2005 | Timm et al. |
| 2005/0262911 A1 | 12/2005 | Dankowicz et al. |
| 2006/0058792 A1 | 3/2006 | Hynes |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2007/0227216 A1 | 10/2007 | Schalliol |
| 2007/0288030 A1 | 12/2007 | Metzger et al. |
| 2008/0086127 A1 | 4/2008 | Patterson et al. |
| 2008/0114370 A1 | 5/2008 | Schoenefeld |
| 2008/0161815 A1 | 7/2008 | Schoenefeld et al. |
| 2008/0183214 A1 | 7/2008 | Copp et al. |
| 2008/0255564 A1 | 10/2008 | Michelson |
| 2008/0257363 A1 | 10/2008 | Schoenefeld et al. |
| 2008/0275452 A1 | 11/2008 | Lang et al. |
| 2008/0287954 A1 | 11/2008 | Kunz |
| 2008/0306552 A1 | 12/2008 | Winslow |
| 2008/0312659 A1 | 12/2008 | Metzger et al. |
| 2008/0319491 A1 | 12/2008 | Schoenefeld |
| 2009/0024131 A1 | 1/2009 | Metzger |
| 2009/0076555 A1 | 3/2009 | Lowry et al. |
| 2009/0087276 A1 | 4/2009 | Rose |
| 2009/0088674 A1 | 4/2009 | Caillouette |
| 2009/0088761 A1 | 4/2009 | Roose et al. |
| 2009/0088763 A1 | 4/2009 | Aram |
| 2009/0093816 A1 | 4/2009 | Roose et al. |
| 2009/0099567 A1 | 4/2009 | Zajac |
| 2009/0105760 A1 | 4/2009 | Frey |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2009/0326537 A1 | 12/2009 | Anderson |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100193 A1 | 4/2010 | White |
| 2010/0152782 A1 | 6/2010 | Stone et al. |
| 2010/0185204 A1 | 7/2010 | Buttermann et al. |
| 2010/0191244 A1 | 7/2010 | White et al. |
| 2010/0217270 A1 | 8/2010 | Polinski et al. |
| 2010/0217336 A1 | 8/2010 | Crawford |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0046628 A1 | 4/2011 | Jamali |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |

(56) References Cited

U.S. PATENT DOCUMENTS

| | | |
|---|---|---|
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2011/0319745 A1 | 12/2011 | Frey |
| 2012/0041445 A1 | 2/2012 | Roose |
| 2012/0130434 A1 | 5/2012 | Stemniski et al. |
| 2012/0150243 A9 | 6/2012 | Crawford et al. |
| 2012/0179259 A1 | 7/2012 | McDonough et al. |
| 2012/0215315 A1 | 8/2012 | Hochschuler et al. |
| 2012/0226283 A1 | 9/2012 | Meridew |
| 2012/0245587 A1 | 9/2012 | Fang |
| 2013/0006251 A1 | 1/2013 | Aram et al. |
| 2013/0053854 A1 | 2/2013 | Schoenefeld et al. |
| 2013/0110174 A1 | 5/2013 | Marik |
| 2013/0123850 A1 | 5/2013 | Schoenefeld et al. |
| 2013/0218163 A1 | 8/2013 | Frey |
| 2014/0137618 A1 | 5/2014 | Isaacs |
| 2014/0350614 A1 | 11/2014 | Frey |
| 2014/0379032 A1 | 12/2014 | Hennard |
| 2015/0047410 A1 | 2/2015 | Petit et al. |
| 2015/0127053 A1 | 5/2015 | Maruenda Paulino et al. |
| 2015/0297249 A1 | 10/2015 | Catanzarite |
| 2016/0030067 A1 | 2/2016 | Frey et al. |
| 2016/0270802 A1 | 9/2016 | Fang et al. |
| 2017/0215857 A1 | 8/2017 | D'Urso |
| 2017/0312032 A1 | 11/2017 | Amanatullah |
| 2018/0082480 A1 | 3/2018 | White |
| 2018/0168740 A1 | 6/2018 | Ryan |
| 2018/0271602 A1 | 9/2018 | Frey |
| 2020/0138519 A1 | 5/2020 | Frey |
| 2020/0360105 A1 | 11/2020 | Frey |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101390773 B | 11/2010 |
| CN | 101953713 | 1/2011 |
| CN | 101953713 B | 5/2012 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EM | 006192001-001 | 4/2019 |
| EM | 006192001-002 | 4/2019 |
| EM | 006192001-003 | 4/2019 |
| EM | 006192001-004 | 4/2019 |
| EM | 006192001-005 | 4/2019 |
| EM | 006192001-006 | 4/2019 |
| EP | 0908836 A2 | 4/1999 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 2006-528533 | 12/2006 |
| JP | 2008-514362 | 5/2008 |
| JP | 2012-143379 | 8/2012 |
| JP | D1508406 | 10/2014 |
| KR | 200382165 Y1 | 4/2005 |
| WO | WO2001037728 | 8/2002 |
| WO | WO2004071314 | 8/2004 |
| WO | WO2006039266 | 4/2006 |
| WO | WO2007145937 | 12/2007 |
| WO | WO2008027549 | 3/2008 |
| WO | WO2009004625 | 1/2009 |
| WO | WO2009035358 | 3/2009 |
| WO | WO2006017641 | 4/2009 |
| WO | WO2008157412 | 4/2009 |
| WO | WO2009129063 | 10/2009 |
| WO | WO2009105106 | 12/2009 |
| WO | WO2010033431 | 3/2010 |
| WO | WO2010148103 | 12/2010 |
| WO | WO2011041398 | 4/2011 |
| WO | WO2011080260 | 7/2011 |
| WO | WO2011106711 | 9/2011 |
| WO | WO2011109260 | 9/2011 |
| WO | WO2012082164 | 6/2012 |
| WO | WO2012152900 | 11/2012 |
| WO | WO2013041618 | 3/2013 |
| WO | WO2013104682 | 7/2013 |
| WO | WO2013169674 | 11/2013 |
| WO | WO2013173700 | 11/2013 |
| WO | WO2014070889 | 5/2014 |
| WO | WO2014088801 | 6/2014 |
| WO | WO2014090908 | 6/2014 |
| WO | WO2014095853 | 6/2014 |
| WO | WO2014143762 | 9/2014 |
| WO | WO2014198279 | 12/2014 |
| WO | WO2016148675 | 9/2016 |

OTHER PUBLICATIONS

Dai et al. "Surgical treatment of the osteoporotic spine with bone cement-injectable cannulated pedicle screw fixation: technical description and preliminary application in 43 patients," Clinics, Feb. 2015, vol. 70, No. 2, pp. 114-119.

Examination Report for IN201617045149. Jun. 12, 2020. 5 pages.

Examination Report for IN20182701734. Jun. 23, 2020. 6 pages.

Examination Report No. 1 for AU2016338436. Sep. 22, 2020. 6 pages.

Examiner Requisition for CA3001898. Jan. 7, 2020. 3 pages.

Extended Search Report for European Patent Application No. 11804191.2, dated May 7, 2015. 8 pages.

Extended Search Report for European Patent Application No. 13778164.7, dated Feb. 17, 2016. 10 pages.

Hong et al. "Binder-jetting 3D printing and alloy development of new biodegradable Fe—Mn—Ca/Mg alloys," Acta Biomaterialia, Nov. 2016, vol. 45, pp. 375-386 (Abstract only) 4 pages.

International Preliminary Report on Patentability for International (PCT) Patent Application No. PCT/US11/42412 mailed Jan. 17, 2013, 7 pages.

International Preliminary Report on Patentability for International Patent Application No. PCT/US2013/036535, mailed Oct. 30, 2014, 7 pages.

International Preliminary Report on Patentability for International Patent Application No. PCT/US2014/041379, mailed Dec. 17, 2015, 6 pages.

International Preliminary Report on Patentability for International Patent Application No. PCT/US2015/032356, mailed Dec. 15, 2016, 7 pages.

International Search Report and Written Opinion for International Patent Application No. PCT/US11/42412 mailed Nov. 8, 2011.

International Search Report and Written Opinion for International Patent Application No. PCT/US15/32356, mailed Oct. 28, 2015, 10 pages.

International Search Report and Written Opinion for International Patent Application No. PCT/US2013/036535, mailed Jun. 26, 2013, 8 pages.

International Search Report and Written Opinion for International Patent Application No. PCT/US2014/041379, mailed Oct. 28, 2014, 7 pages.

International Search Report and Written Opinion for International Patent Application No. PCT/US2016/056970, mailed Mar. 10, 2017, 13 pages.

Introducing IntelliSense Drill Technology®, McGinley Orthopaedic Innovations, 1 page, [captured Feb. 29, 2016 from: http://web.archive.org/web/20160229042028/http://www.mcginleyorthopaedicinnovations.com/index.php?/pages/drill].

Jakus et al. "Hyperelastic "bone": A highly versatile, growth factor-free, osteoregenerative, scalable, and surgically friendly biomate-

(56) References Cited

OTHER PUBLICATIONS rial," Science Translational Medicine, Sep. 2016, vol. 8, No. 358, pp. 358ra127 (Abstract only) 5 pages.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Notice of Allowance for U.S. Appl. No. 13/172,683 mailed Apr. 23, 2014., 7 pages.
Notice of Allowance for U.S. Appl. No. 13/841,069, mailed Sep. 18, 2014. 7 pages.
Notice of Allowance for U.S. Appl. No. 14/298,624, mailed Oct. 7, 2015. 7 pages.
Notice of Allowance for U.S. Appl. No. 14/883,299, mailed Mar. 20, 2017. 12 pages.
Notice of Allowance for U.S. Appl. No. 29/409,734, mailed May 11, 2012. 8 pages.
Notice of Allowance for U.S. Appl. No. 29/427,918, mailed Oct. 15, 2012. 9 pages.
Notice of Allowance for U.S. Appl. No. 29/432,668 mailed Nov. 27, 2013. 11 pages.
Notice of Allowance for U.S. Appl. No. 29/476,699, mailed Oct. 2, 2015. 8 pages.
Notice of Allowance for U.S. Appl. No. 29/476,705, mailed Oct. 7, 2015. 8 pages.
Notice of Allowance for U.S. Appl. No. 29/476,709, mailed Nov. 6, 2015. 8 pages.
Notice of Allowance for U.S. Appl. No. 29/496,231, mailed Jul. 23, 2015. 10 pages.
Notice of Allowance for U.S. Appl. No. 29/538,633, mailed Jan. 6, 2016. 10 pages.
Notice of Allowance with English Translation for Japan Patent Application No. 2013-518663, mailed Dec. 8, 2015. 4 pages.
Notice off Allowance with English Translation for Japan Patent Application No. 2015-507078, mailed Jan. 10, 2017. 4 pages.
Office Action in BR112018007443-8. Jun. 9, 2020. 4 pages.
Official Action for Australian Patent Application No. 2011276468 dated Apr. 10, 2013, 3 Pages.
Official Action for Canada Patent Application No. 2,802,094, dated Feb. 14, 2017, 4 pages.
Official Action for Canada Patent Application No. 2,914,005, mailed Feb. 3, 2017, 3 pages.
Official Action for China Patent Application No. 201180029692.7, mailed Oct. 8, 2014 12 pages.
Official Action for European Patent Application No. 11804191.2, dated Feb. 17, 2017, 5 pages.
Official Action for U.S. Appl. No. 13/172,683, mailed Feb. 24, 2014, 10 pages.
Official Action for U.S. Appl. No. 13/172,683, mailed Sep. 10, 2013 7 pages.
Official Action for U.S. Appl. No. 13/841,069 mailed Jul. 8, 2014, 6 pages.
Official Action for U.S. Appl. No. 13/841,069, mailed Jul. 31, 2014 9 pages.
Official Action for U.S. Appl. No. 14/298,634, mailed Apr. 27, 2015 8 pages.
Official Action for U.S. Appl. No. 14/298,634, mailed Jul. 7, 2015 6 pages.
Official Action with English Translation for China Patent Application No. 201380030638.3, dated Feb. 4, 2017. 6 pages.
Official Action with English Translation for China Patent Application No. 201380030638.3, dated May 25, 2016. 11 pages.
Official Action with English Translation for Japan Patent Application No. 2013-518663, mailed May 12, 2015. 4 pages.
Official Action with English Translation for Russia Patent Application No. 2014143528/14, dated Jan. 13, 2017. 8 pages.
Owen et al. "Rapid prototype patient-specific drill template for cervical pedicle screw placement." Computer Aided Surgery, Sep. 2007, vol. 12, No. 5, pp. 303-308 (Abstract Only).
Partial Search Report for European Patent Application No. 11804191.2, dated Jan. 20, 2015 6 pages.
Ryken et al. "Image-based drill templates for cervical pedicle screw placement Laboratory investigation," Journal of Neurosurgery, Jan. 2009, vol. 10, No. 1 (Abstract Only).
Translated Office Action from Japanese Patent Application No. 2018-519856. Oct. 6, 2020. 3 pages.
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
S. Lu, et al., A Novel Computer-Assisted Drill Guide Template for Lumbar Pedicle Screw Placement: A Cadaveric and Clinical Study, 5 Int. J. Med. Robotics Comput. Surg. 184-191 (2009).
S. Lu, et al., A Novel Patient-Specific Template for Cervical Pedicle Screw Placement, 34 Spine E9595-E964 (2009).
Lu et al., A novel computer-assisted drill guide template for placement of C2 laminar screws, E. Spine J., 1379-1385 (2009).
T. Ryken, et al., Image-Based Drill Templates for Cervical Pedicle Screw Placement, 10 J. Neurosurg. Spine 21-26 (2009).
Owen et al., Rapid Prototype Patient Specific Drill Template for Cervical Pedicle Screw Placement (2007).
K. Radermacher, et al., Technique for Better Execution of CT Scan Planned Orthopedic Surgery on Bone Structures, Comp. Assisted Radiology: Proceedings of the Int'l Symposium on Comp. & Comm. Sys. for Image Guided Diagnosis & Therapy (1995).
International Patent Application Publication No. WO 1993/025157, filed by K. Radermacher et al. on Jun. 17, 1993.
K. Radermacher, et al., Image Guided Orthopedic Surgery Using Individual Templates, Image Guided Orthopedic Surgery (1997).
K. Radermacher, et al., Computer Assisted Orthopaedic Surgery With Image Based Individual Templates, 354 Clinical Orthopaedics & Related Res. 28 (1998).
Van Brussel et al., Medical Image-Based Design of an Individualized Surgical Guide for Pedicle Screw Insertion (1996).
Birnbaum et al., Computer-Assisted Orthopedic Surgery with Individual Templates and Comparison to Conventional Operation Method (2001).
Berry et al., Personalized image-based templates for intra-operative guidance, J. Engineering in Medicine, 219:111-118 (2005).
Salako, et al., "Feasibility Study of Patient-Specific Surgical Templates for Fixation of Pedicle Screws," Stud Health Technol Inform. 2002;88:419-22 (2002).
Zhang et al., Application of Navigation Template to Fixation of Sacral Fracture Using Three-Dimensional Reconstruction and Reverse Engineering Technique (2009), which was published on Aug. 2009.

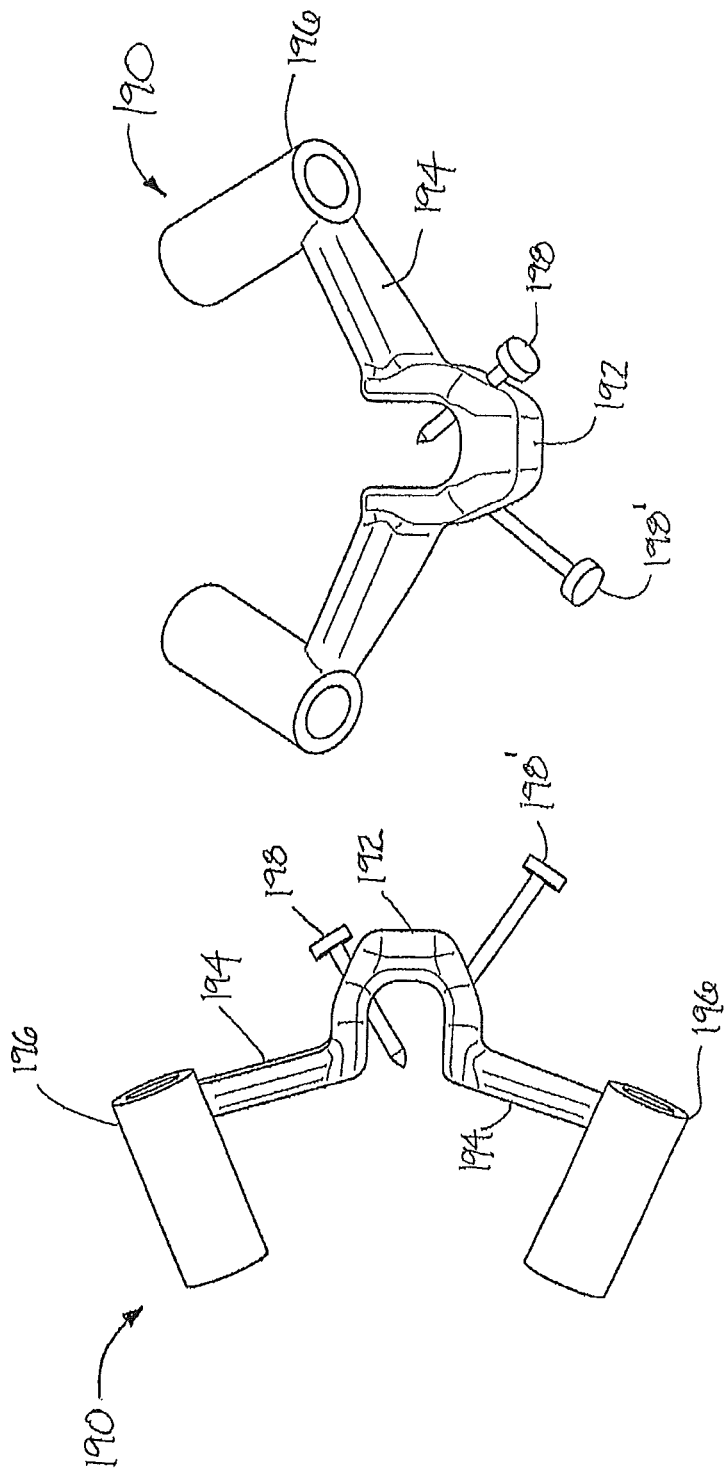

Insert Diameter for 4.5 mm Tap

Insert Diameter for 1/8" Drill Bit

FIG. 33A
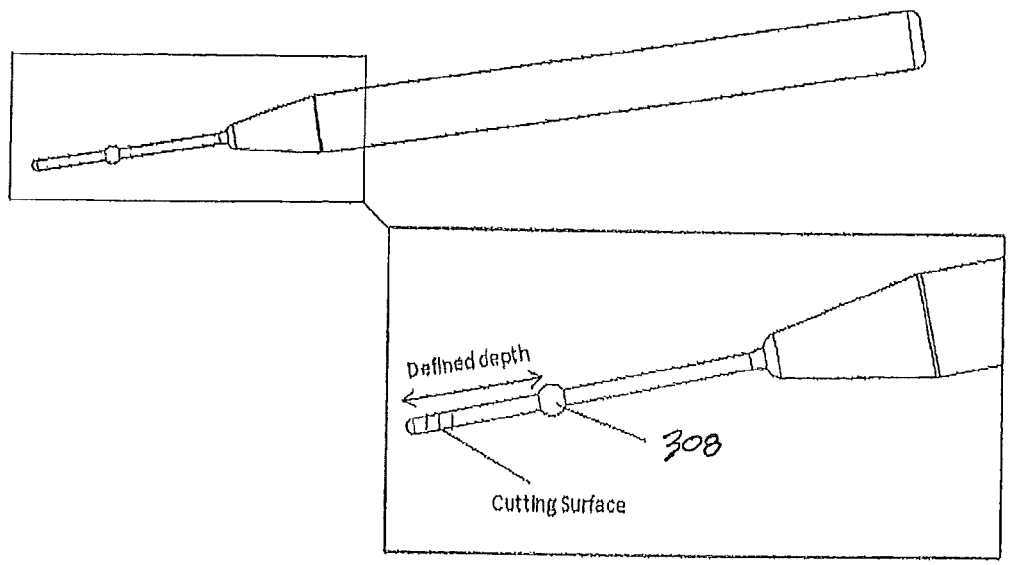
FIG. 33B
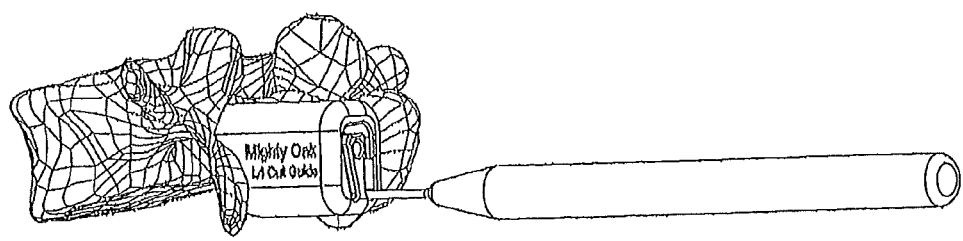
FIG. 33C

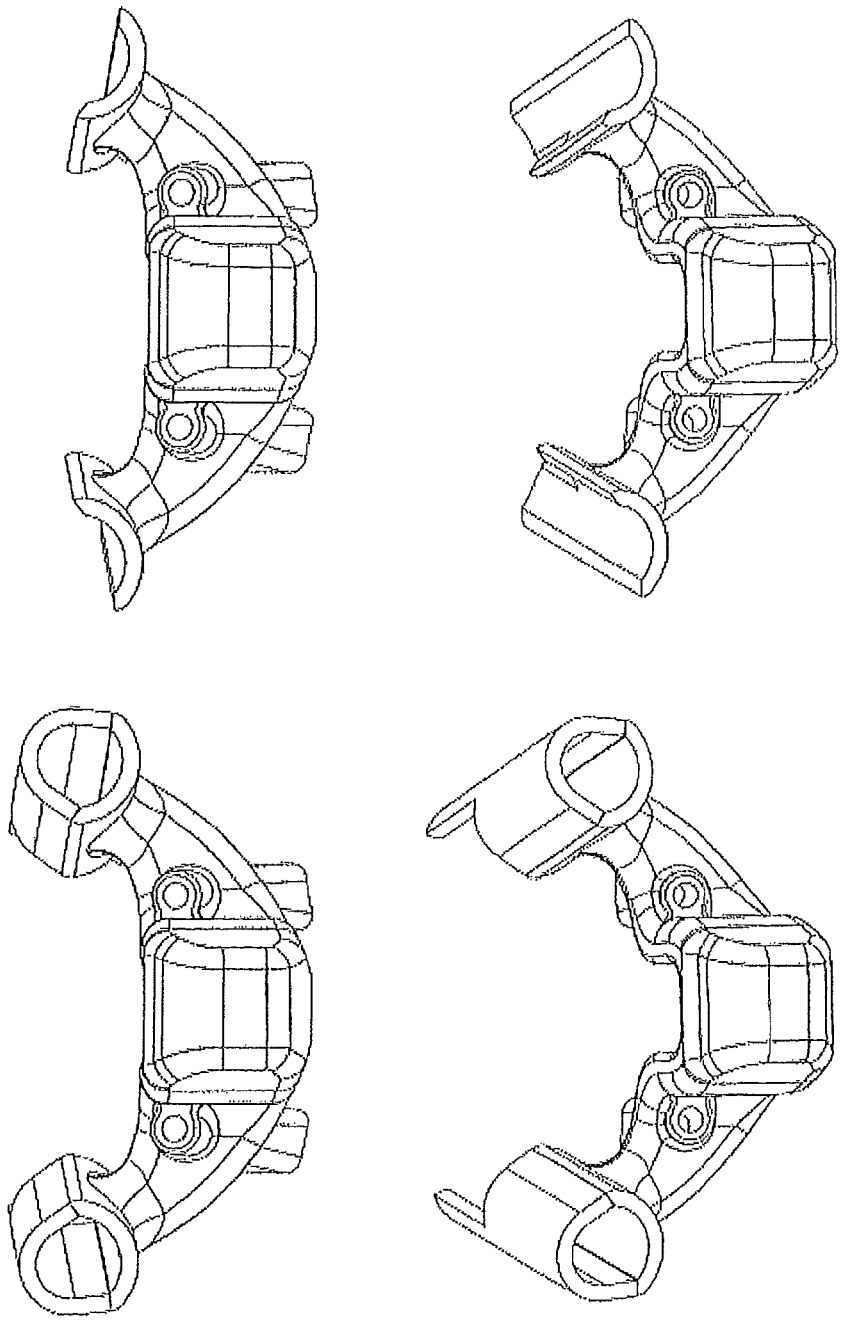
FIGURE 40 A-D

PATIENT-MATCHED APPARATUS FOR USE IN SPINE RELATED SURGICAL PROCEDURES AND METHODS FOR USING THE SAME

CROSS REFERENCE TO RELATED APPLICATIONS

This application is a continuation of U.S. patent application Ser. No. 17/402,512 filed on Aug. 14, 2021, now issued as U.S. Pat. No. 11,806,197, which in turn is a continuation of U.S. patent application Ser. No. 16/831,215 filed on Mar. 26, 2020, now issued as U.S. Pat. No. 11,633,254, which claims priority under 35 U.S.C. § 119(e) to U.S. Provisional Patent Application Ser. No. 62/823,911 filed Mar. 26, 2019. U.S. patent application Ser. No. 16/831,215 is a also continuation-in-part of U.S. patent application Ser. No. 16/598,861 filed on Oct. 10, 2019, now issued as U.S. Pat. No. 11,376,073, which claims priority under 35 U.S.C. § 119(e) to U.S. Provisional Application Ser. No. 62/743,661 filed Oct. 10, 2018, and which is also a continuation-in-part of U.S. patent application Ser. No. 15/997,404 filed Jun. 4, 2018, now issued as U.S. Pat. No. 11,039,889, which is a continuation-in-part of U.S. patent application Ser. No. 15/416,975 filed on Jan. 26, 2017, now issued as U.S. Pat. No. 9,987,024, which in turn is a continuation-in-part of U.S. patent application Ser. No. 14/883,299 filed Oct. 14, 2015, now issued as U.S. Pat. No. 9,642,633, and claims priority under 35 U.S.C. § 119(e) to U.S. Provisional Patent Application 62/373,855 filed Aug. 11, 2016, to U.S. Provisional Patent Application Ser. No. 62/362,440 filed Jul. 14, 2016, and to U.S. Provisional Patent Application Ser. No. 62/287,134 filed Jan. 26, 2016. U.S. patent application Ser. No. 14/883,299 is a continuation-in-part of U.S. patent application Ser. No. 14/298,634, filed Jun. 6, 2014, now issued as U.S. Pat. No. 9,198,678 on Dec. 1, 2015, and claims priority under 35 U.S.C. § 119(e) to U.S. Provisional Application Ser. No. 62/162,466, filed May 15, 2015. U.S. patent application Ser. No. 14/298,634 claims priority to U.S. Provisional Patent Application Nos. 61/877,837 filed Sep. 13, 2013, 61/845,463 filed Jul. 12, 2013, and 61/832,583 filed Jun. 7, 2013, and is a continuation-in-part of U.S. patent application Ser. No. 13/841,069 filed Mar. 15, 2013, now issued as U.S. Pat. No. 8,870,889, which claims priority under 35 U.S.C. § 119(e) to U.S. Provisional Patent Application Nos. 61/625,559 filed Apr. 17, 2012, 61/393,695 filed Oct. 15, 2010, and 61/359,710 filed Jun. 29, 2010. U.S. patent application Ser. No. 13/841,069 is also a continuation in part of U.S. patent application Ser. No. 13/172,683 filed Jun. 29, 2011, now issued as U.S. Pat. No. 8,758,357. U.S. patent application Ser. No. 13/172,683 claims priority to U.S. Provisional Patent Application Nos. 61/393,695 filed Oct. 15, 2010, and 61/359,710 filed Jun. 29, 2010. U.S. patent application Ser. No. 15/997,404 also claims priority under 35 U.S.C. § 119(e) to U.S. Provisional Patent Application Ser. No. 62/628,626 filed Feb. 9, 2018. The entireties of these applications and patents are incorporated by reference herein.

FIELD OF THE INVENTION

The present disclosure generally relates to the field of medical devices, and more specifically toward systems for use with a patient-specific or patient-matched surgical device based on the patient's unique anatomical features for use in cervical and thoracic areas of the human spine. The present disclosure also relates to methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of orthopedic screws or other fixation devices in a patient's boney anatomy is well accepted amongst surgeons who treat various orthopedic pathologies. Although the performance of various screw constructs has become predictable, there are still multiple challenges with the placement and insertion of the orthopedic screws or other fixation devices. The challenges occur, for example, when a surgeon is unable to reference boney landmarks due to previous surgery or when the patient's anatomy is irregular in shape, or when a particular trajectory for insertion of the screws (or other fixation devices) is impeded by anatomical obstructions.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a customized surgical guide and/or implant based on the dynamic nature of the anatomical structures the customized guide/implant is designed to associate with. This data, while currently used by surgeons in surgery planning, is largely unused for creating a customized set of instruments or other surgical devices that are designed to complement the patient's unique anatomy.

In addition, virtual reality and/or augmented reality systems (collectively referred to as "AR" in this disclosure) have provided advantages to surgeons with respect to surgical planning and in particular the ability of surgeons to visual the orientation and placement of orthopedic implants and/or instruments. The surgeon would therefore benefit from the enhanced ability to merge AR capabilities with patient-specific surgical devices and/or equipment, as well as customized manufacturing and placement of patient-specific guides/implants. While various types of augmented reality (AR) systems are provided in the prior art, several are not applicable or usable with the current state of surgical equipment, including those AR systems that pertain to driving assistance for vehicles, games, and entertainment attractions. In addition, different localization methods may be used with prior art AR systems, such as sensor-based localization methods relying on the use of many sensors. As another example, certain AR systems rely on a global positioning system (GPS) sensor and/or an inertial measurement unit (IMU) sensor to verify a location and a direction of an object. When high accuracy is required, a sensor-based localization method requires a specific (and often expensive) sensor with a high degree of accuracy, but is not practical in surgical settings. Furthermore, many prior art vision-based localization methods rely on specific camera information to acquire highly precise information, yet are difficult to use in a surgical environment.

Specific surgical procedures are often performed in the spinal and/or cephalad region of a patient. The procedures performed in these areas are often designed to stop and/or eliminate all motion, including by removal and/or destruction of some or all of the boney anatomy in the patient's boney anatomy and/or implantable fixation devices (i.e., plates or screws) for limiting movement of the boney anatomy of the particular patient. By eliminating movement, pain and degenerative disease may be reduced or avoided.

A significant danger of performing operations on a patient's orthopedic anatomy, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also obstruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art procedures on the spine, including MIS procedures.

As described herein, the prior art fails to teach a system for creating patient-specific or patient-matched surgical apparatus, based on the data set derived from the MRI or CT scan, for use with robotic and AR systems. The use of the patient-specific data set for a vertebral or other anatomic body of a particular patient may allow a surgeon to accommodate for subtle variations in the position and orientation of a screw, plate or other bone anchor to avoid particular boney anatomy or irregularities in the positioning and alignment of the adjoining vertebral bodies.

As another example, the use of these data sets may also assist a surgeon in selecting a desired trajectory for an implantable device so as to avoid sensitive anatomical features of a particular patient or to secure a bone anchoring device in a particular area of desired bone density during an actual procedure. The use of patient-specific data sets further permits the surgeon to avoid mistakes by creating customized tools and instruments, which may comprise orientation, end-stops or other safety related features to avoid over-torque and/or over-insertion of any implantable devices. The use of patient-specific data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure and/or patient-specific apparatus that is adapted to conform to a plurality of anatomical features of a particular patient and that otherwise assists a surgeon in completing the surgical procedure(s) safely and efficiently. It is also advantageous to provide a procedure and/or apparatus that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures, particularly those procedures associated certain cervical and/or certain thoracic vertebrae. The systems and methods described herein incorporate a patient's unique morphology, which may be derived from capturing MRI, CT, or other data to derive one or more "Patient Matched" apparatus, which comprises complementary surfaces based on a plurality of data points from the MRI, CT or other anatomical data. Each "Patient Matched" apparatus is matched and oriented around the patient's own anatomy, and is preferably configured to incorporate specific and/or desired insertional trajectories (which may be verified in a pre-operative setting using 3D CAD software, such as the software disclosed in WO 2008027549, which is incorporated by reference herein in its entirety). According to one embodiment described herein, other apparatus used during the surgical procedure may facilitate the orientation and/or placement of one or more implants, including plates, screws, fixation devices, etc.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Various surgical procedures using the apparatus and systems described herein may be performed with sequential or simultaneous introduction of rods, pins, plates, screws or other surgical devices into adjacent boney anatomy to join various portions of, for example, cervical vertebrae of a particular patient. Such procedures often require introduction of additional tools to prepare a site for implantation. These tools may include drills, drill guides, debridement tools, irrigation devices, vises, clamps, cannula, and other insertion/retraction tools.

Orthopedic and other surgeries may be performed by a number of different procedures, as opposed to conventional surgical procedures and methods, which typically require cutting of muscles, removal of bone, and retraction of other natural elements. During a MIS procedure, for example, including procedures using the apparatus of the present invention, a less destructive approach to the patient anatomy is carried out by using retractor tubes or portals, which take advantage of anatomy and current technology to limit the damage to intervening structures.

In typical surgical procedures, skeletal landmarks are established fluoroscopically and a small incision is made over the landmark(s). According to various methods known in the prior art, a series of dilators may be applied until one or more cannula is placed over the anatomic structure. In some procedures, a microscope is then placed over the operative site to provide illumination and magnification with a three-dimensional view of the anatomical site to ensure that the surgeon is able to accurately locate the desired patient anatomy and properly position and orient any tool, instrument or other surgical device used during the procedure. The microscope, however, is an expensive and unwieldy device requiring uncomfortable gyrations of the surgeon's back and neck in order to gain the necessary view and is a nuisance to drape (a large, sterile plastic bag has to be placed over the eight-foot-tall structure). The use of adequate illumination is also difficult to direct due to the size of the microscope.

The customized and integrated matching aspects of this presently disclosed system provides an advantage over the prior art, in particular by providing a plurality of interlocking and/or matching points for each apparatus, which are easily or efficiently registerable and positionable using robotic and AR systems, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises, but is not limited to: (1) obtaining data associated with a patient's anatomy; (2) converting the data obtained to a 3-dimensional data set(s); (3) determining at least one trajectory or path for facilitating a surgical procedure to be performed on the patient; (4) determining at least one surface associated with the patient's anatomy; (5) generating a 3-dimensional representation of the customized surgical device or instrument, which incorporates the at least one trajectory of path and a matching surface to the at least one surface associated with the patient's anatomy; (6) fabricating the customized surgical device or instrument using the 3-dimensional representation; (7) registering at least one marker on the customized surgical device with a robotic or an AR system; and (8) positioning the customized surgical device on the patient's anatomy utilizing the at least one surface associated with the patient's anatomy and the at least one marker.

According to embodiments, the at least one trajectory or path may be a pedicle screw trajectory, a cortical bone trajectory, a cortical trajectory, a sacral pedicle trajectory, a sacral alar trajectory, an S2-alar-iliac trajectory, an iliac trajectory, a transarticular trajectory, a lateral mass trajectory, a translaminar trajectory, a transcondylar trajectory, a cervical pedicle screw trajectory, a sub axial lateral mass screw trajectory, a transpedicular screw trajectory, a pars screw trajectory, an occipitocervical screw trajectory, an occipital screw trajectory and an occipital condyle C1 screw trajectory.

According to this aspect described above, the method steps may further comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from a radiographic imaging machine, an ultrasonic machine, a bone density scanning machine, or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc. The apparatus may comprise one or more stops located within the pathways for preventing a tool, instrument or implant from advancing beyond a predetermined distance.

In embodiments, the apparatus is a surgical guide that is oriented in at least one trajectory. The trajectory may be one of: (1) a cervical pedicle screw trajectory; (2) a pedicle screw trajectory; (3) a cortical or cortical bone trajectory; (4) a sacral pedicle trajectory; (5) a sacral alar trajectory; (6) an S2-alar-iliac trajectory; (7) an iliac trajectory; (8) a transarticular trajectory; (9) a lateral mass trajectory; (10) a translaminar trajectory; (11) a transcondylar trajectory; and (12) an occipital trajectory (for example, during an operation on a patient's occipital or surrounding cervical anatomy).

One aspect of the present disclosure relates to a customized apparatus, comprising: a central portion of the apparatus, which comprises a first and a second extension; at least a first surface configured to be complementary to a predetermined portion of an anatomical feature; and at least a second surface distinct from the at least a first surface that is configured to be complementary to another predetermined portion of an anatomical feature; at least one marker in communication with the augmented reality system; wherein a patient-matched connection between the apparatus and the patient is established by placement of the at least a first surface on the predetermined portion of an anatomic feature and placement of the at least a second surface on the another predetermined portion.

One aspect of the present disclosure is a patient-specific guide designed to fit on one or more lumbar, cervical and/or thoracic vertebra(e) of a patient. Another aspect is a patient-specific guide designed to fit at least partially on the occipital bone of the cephalad. According to this embodiment, the guide is designed to be placed in a mating configuration on the bone to provide location, trajectory, and depth of pilot holes for subsequent alignment/placement of, for example, a screw and/or a plate. In certain alternate embodiments, the guide may be used to both align and "carry" the plate. Alternatively, the patient-specific guide may be removable once the plate or other implant is adequately positioned on the patient's boney anatomy.

In another aspect, the present disclosure relates to a patient-specific guide, comprising: a body; a first cannula oriented in a predetermined trajectory; a second cannula oriented in a predetermined trajectory; a first patient distal end of the first cannula; wherein at least a portion of the first cannula and the second cannula comprise a plurality of patient-specific contours derived from patient-specific data obtained from the patient and configured to mate with patient-specific features; and wherein the predetermined trajectory of the first cannula and the second cannula are determined at least in part from bone density data obtained from the patient.

In embodiments, patient-specific guides described herein may be used with various orientation or registration markers for identification by a robot. Certain guides may comprise an embedded chip, circuit or equivalent with presurgical planning information, which may be read by a machine and deliver specific instructions to a robotic surgical device, for example. Such patient-specific guides may be used on multiple levels of a patient's spine that are impacted by a particular surgical procedure, and thereby provide markers for registration and orientation without having to rescan the patient throughout the surgery. The robotic device may view the patient and position of the patient's unique anatomy through the identification of the markers, and thereby more rapidly align instrumentation controlled by the robotic equipment.

In embodiments, the patient-specific guides described herein comprises a locating feature for a robot or other autonomous device to align the guide to a vertebra in space, for example. With multiple locating guides placed on a patient's vertebra, a robot can drill into the vertebra, affix an orientation tool, and/or orient vertebra relative to each other to meet pre-surgically planned spinal alignment. Pre-surgically planned spinal alignment may also be matched to one or more pre-bent rods, minimizing surgical time. In other embodiments, the robot or other autonomous device may be configured to perform an osteotomy with known locations of vertebra relative to each other.

In embodiments, the surgical devices described herein may be used with an AR system or associated simulation device. In one embodiment, the AR capabilities are provided in conjunction with a physical guide, while in other embodiments the capabilities are provided in conjunction with a "virtual" guide. In one embodiment, the surgical device is configured as a patient-specific pedicle screw placement guide is for use with a surgical instrument or implantable device. The pedicle screw placement guide is preferably adapted to guide intra-operative placement of pedicle screws that are used to anchor a pedicle screw spinal system onto target portion of a patient's anatomy. In one embodiment, the target portion of the patient's anatomy is a posterior element of the patient's spine, including lumbar, interbody and cervical portions of a patient's spine.

Another aspect of the present disclosure relates to a system for performing one or more surgical procedures facilitated by a computer-aided navigational apparatus, comprising: at least one robotic apparatus; a processor in communication with the at least one robotic apparatus; a patient-specific apparatus configured to be placed on at least one patient-specific feature; at least one marker that is positioned in a known location relative to patient anatomy and configured to transmit positional information to the processor; wherein the processor is configured to receive and relay the positional information received from the at least one marker to determine the location and orientation of the at least one robotic apparatus relative to patient anatomy.

In another embodiment, the pedicle screw placement guide utilizes anatomic landmarks that are identified pre-operatively by a medical imaging scan of the patient, as well as markers that are registerable using a robotic or AR system. Optionally, the medical imaging scan of the patient may include one or more of: an MRI scan, a CT scan, and an x-ray scan. Data obtained from the medical imaging scan may be used to generate a pre-operative plan for the patient and facilitate the operation for the specific patient. The pedicle screw placement guide is configured to be used in a surgical procedure to place a pedicle screw in a pre-operatively determined orientation or trajectory.

According to yet another aspect of the present disclosure, a preconfigured surgical template is disclosed, which comprises one or more guides for receiving at least one plate. According to this embodiment, the template further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are preferably oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed. The method includes, but is not limited to: (1) collecting data from the patient corresponding to the patient's unique anatomy; (2) creating a model of the template from the data collected, the model comprising a plurality of matching surfaces to the patient's unique anatomy; (3) providing data associated with model to fabrication machinery; (4) rapidly generating the template to comprise the plurality of matching surfaces and further comprising at least one additional matching surface corresponding to at least one tool or instrument used in the surgical operation; and (5) generating a permanent device based on the template for use in the surgical operation.

In one embodiment of the present disclosure, the model is a digital model. In another embodiment of the present disclosure, the model is a physical model.

It is another aspect of the present disclosure to provide a patient-specific guide for use in a surgical procedure. The guide includes, but is not limited to: (1) a body having a proximal portion and a distal portion; (2) at least one cannula comprising a proximal and distal portion and a bore oriented in a direction determined from the anatomical features of a patient, the bore adapted to guide an instrument or a fixation device in a desired trajectory; and (3) a surface of the guide including patient-specific contours determined from the patient's anatomy and configured to contact and substantially conform to at least a first subcutaneous anatomic feature of the patient.

In certain embodiments, the guide further comprises one or more surfaces configured to avoid potentially damaging contact between the surfaces of the guide and surrounding tissue. In one embodiment, the surface in substantially planar and acts a shield to soft tissue on the opposite side of the spinous process as the at least one cannula. In embodiments, the shielding surface of the guide may be removable or adjustable to account for specific tissue the surgeon or health professional preferences.

In one embodiment, the bore of the at least one cannula may have different diameters and/or trajectories between one guide and another. In one embodiment, the bore is directed in a first predetermined trajectory. In another embodiment, the bore(s) are directed in a first and a second predetermined trajectory. In another embodiment, the bore(s) are directed in a plurality of trajectories, each different from the others.

In still another embodiment, the body further comprises a second bore that is oriented in a direction for placement of a fixation device. The guide may further comprise a second surface including patient-specific contours determined from the patient's anatomy and configured to contact and substantially conform to a second anatomic feature of the patient. Additionally, the body may optionally include at least one extension from the body, the at least extension including a second surface including patient-specific contours determined from the patient's anatomy and configured to contact and substantially conform to a second anatomic feature of the patient.

In one embodiment, at least one surface of the apparatus, such as the surface with the patient-specific contours, is adapted to hook at least partially around a specific portion of the patient's anatomy. In another embodiment, at least a portion of the guide is shaped to prevent contact with a portion of the patient's anatomy.

In still another embodiment, the body of the guide comprises a first portion releasably interconnected to a second portion. Optionally, the body may comprise at least two portions. In one embodiment, the portions of the body are adapted to be interconnected together.

In one embodiment, at least a portion of one of the extensions is adapted to hook at least partially around, and substantially conform to, a second anatomic feature of the patient. In one embodiment, at least one of the extensions is adapted to contact a portion of the patient's anatomy that has been altered by a surgical procedure. In another embodiment, at least one of the extensions is adapted to contact an unaltered portion of the patient's anatomy.

The guides and models described herein may comprise one or more of a polymeric material and a metallic material. In another embodiments, the model and/or guide includes at least one patient-matched surface that is substantially congruent to a mating surface of a portion of the patient's anatomy. In one element, the mating surface is a cervical vertebra(e) of a human.

The surgical device may be used in one or more of a minimally invasive surgical procedure and a minimal access procedure. In one embodiment, the surgical device is configured for use in conjunction with a device that employs automated or semi-automated manipulation such that placement of the surgical device with respect to the anatomical feature may be performed remotely by an operator through a computer controller. In another embodiment, the surgical device is identifiable by optical, electronic, or radiological recognition means such that the location and orientation of the surgical device with respect to the anatomical feature is verifiable. In still another embodiment, the surgical device is configured for use in conjunction with a navigation device such that placement of the surgical device with respect to the anatomical feature assists with one or more of registration, stability, and motion tracking by the navigation device.

Incorporated by reference in their entireties are the following U.S. patents and patent applications and international publications directed generally to methods and apparatus related to surgical procedures, thus providing written description support for various aspects of the present disclosure. The U.S. patents and pending applications incorporated by reference are as follows: U.S. Pat. Nos. 9,295,497, 8,758,357, 8,419,740, 8,357,111, 8,298,237, 8,277,461, 8,257,083, 8,214,014, 8,206,396, 8,167,884, 8,159,753, 7,957,824, 7,844,356, 7,658,610, 7,623,902, 7,491,180, 7,235,076, 6,755,839, 6,711,432, 5,201,734, and 3,151,392, U.S. Design Pat. Nos. D705,929, D669,176, D672,038, D618,796, D606,195, D533,664, D532,515, D428,989, D420,132, D412,032, D403,066, and D359,557, and U.S. Pat. Pub. Nos. 2013/0123850, 2013/0053854, 2013/0218163, 2012/0215315, 2012/0179259, 2012/0130434, 2012/0041445, 2011/0319745, 2011/0288433, 2011/0224674, 2011/0218545, 2011/0213376, 2011/0190899, 2011/0184526, 2011/0184419, 2011/0166578, 2011/0160867, 2011/0160736, 2011/0093086, 2011/0093023, 2011/0071533, 2011/0054478, 2011/0046735, 2011/0015639, 2011/0015636, 2010/0324692, 2010/0305700, 2010/0217336, 2010/0217270, 2010/0191244, 2010/0152782, 2010/0100193, 2010/0087829, 2010/0082035, 2010/0049195, 2010/0016984, 2009/0270868, 2009/0254093, 2009/0198277, 2009/0187194, 2009/0138020, 2009/0110498, 2009/0099567, 2009/0093816, 2009/0088763, 2009/0088761, 2009/0088674, 2009/0087276, 2008/0319491, 2008/0312659, 2008/0275452, 2008/0257363, 2008/0183214, 2008/0161815, 2008/0114370, 2007/0288030, 2006/039266, 2006/0241385, 2006/0149375, 2006/0095044, 2006/0084986, 2005/0148843, 2004/0243481, and 2004/0097925. The international publications incorporated by reference are as follows: European Publication No. EP 2168507, and World Intellectual Property Organization Pub. Nos. WO 2013/104682, WO 2013/041618, WO 2012/152900, WO 2011/109260, WO 2011/106711, WO 2011/080260, WO 2011/041398, WO 2010/148103, WO 2010/033431, WO 2009/129063, WO 2008/027549, and WO 2007/145937, and Chinese Publication Nos. CN 201275138, CN 201404283, CN 101390773, and CN 101953713.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention.

Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein. In the drawings:

FIGS. 18-19 are perspective views according to yet another alternative embodiment of the present disclosure;

FIG. 33A is a perspective view according to yet another alternative embodiment of the present disclosure;

FIG. 33B is a perspective view according to the embodiment shown in FIG. 33A;

FIG. 33C is another perspective view according to the embodiment shown in FIG. 33A depicted with the cutting guide of FIG. 32A;

FIGS. 40A-D are additional top plan views of the devices according to the embodiments shown in FIGS. 35-39.

DETAILED DESCRIPTION

As shown in FIGS. 1-40 and described in further detail herein, the present disclosure relates to a novel system and method for design and use of a customized, patient-matched apparatus for use in a diverse number of surgical procedures, particularly those procedures occurring in the cervical and thoracic spine. The apparatus preferably uses a patient's unique morphology, which may be derived from capturing MRI data, CT data, or any other medical imaging device to derive one or more patient-matched elements or components, which comprise complementary surfaces to those encountered during the surgical procedure(s) as derived from a set of data points.

According to various embodiments described herein, the patient-matched apparatus may comprise one or more cannula(e), one or more arms, a tab for grasping the apparatus, and one or more patient-matched surfaces for seating the apparatus on a particular patient's anatomical features. The apparatus may further comprise desired axes and/or insertional trajectories. According to embodiments, the patient-matched apparatus may be further matched with at least one other apparatus used during the surgical procedure. Other features of the disclosure will become apparent after a review of the following disclosures and varying embodiments of the disclosure.

Figure 1:
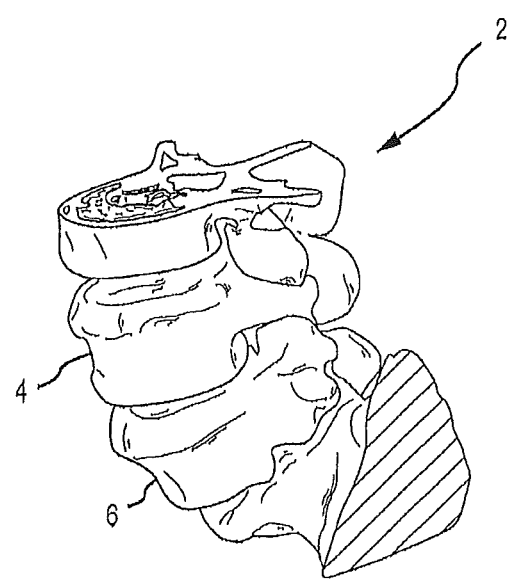
FIG. 1 is a perspective view of a three-dimensional model of a unique grouping of anatomical features from which a set of data points may be derived according to one embodiment of the present disclosure.

Multiple embodiments of a patient-specific apparatus according to certain aspects of the disclosure are depicted in FIGS. 1-40. In embodiments, the apparatus is referred to as a "guide" and is adapted to fit directly to aspects of a patient's anatomy. Referring now to FIG. 1, a perspective view of a three-dimensional model of a unique grouping of anatomical features according to one embodiment of the present disclosure is shown. Here, the model 2 is comprised of multiple vertebral bodies 4, 6 but according to other embodiments may be comprised of any anatomical grouping for a particular patient. Data associated with the model 2 may be captured from a MRI or CT scan or from radiographic images of the patient's corresponding boney anatomy (or alternatively from other data sources). The data, once captured, may be converted using known software tools to a CAD program, where the data set is representative of the model 2 and may be used to provide additional data points for forming the contours, sizes, shapes and orientations of one or more apparatus to be used in the surgical procedure.

According to an alternative embodiment, the data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

Figure 2:
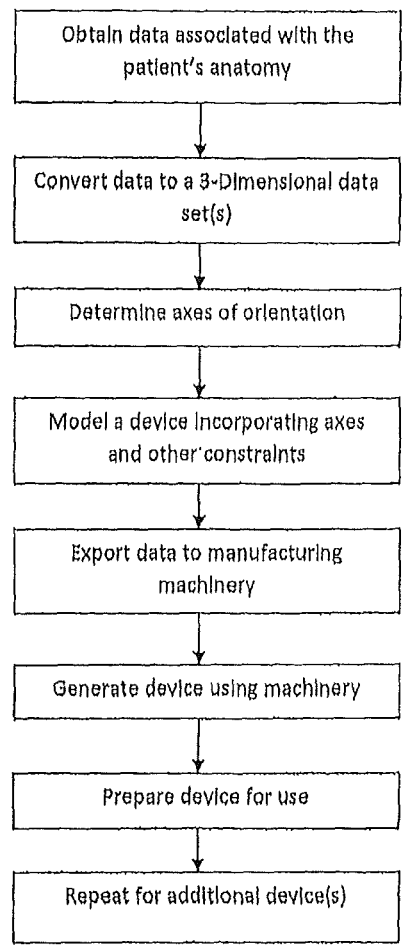
FIG. 2 is a flow chart diagram showing the various steps of performing a method of manufacturing and using an apparatus for facilitating a surgical procedure according to one embodiment of the present disclosure.

FIG. 2 is a flow chart showing the various steps of performing a method of manufacturing an apparatus, according to various embodiments described herein, for use in facilitating a surgical procedure. The method, according to a preferred embodiment, comprises the following steps: A) Obtaining data associated with the patient's anatomy by way of a MRI or CT scan; B) Converting the MRI or CT scan data to a 3-Dimensional data set(s); C) Determining one or more axes of orientation of a device to be constructed for use in facilitating the surgical procedure(s) to be performed on the patient; D) Modeling the device for use in facilitating the surgical procedure(s) using the determined axes and accounting for any other constraints derived from the converted data set(s); E) Generating a prototype of the modeled device by, for example, use of rapid prototyping machinery; and F) Preparing the prototype for use during the surgical procedure(s).

As shown in FIG. 2, the method may comprise additional steps or may be repeated for additional devices used in the surgical procedure. The step of obtaining data is typically performed in a traditional manner, by subjecting the patient to a scan using MRI or CT or other suitable scanning equipment known in the art. The data is then captured by the equipment and may be converted to a 3-Dimensional data set(s) by software or other algorithmic means known in the art, such as by exporting the data into a known modeling software program that allows data to be represented, for example, in CAD format. Once this data is converted, a device may be modeled to complement the data set(s) and oriented by one or more axes determined by the surgeon either before or through observation of the data set(s) from the initial scan of the patient's anatomy.

The method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc. The prototype may be generated using known rapid prototyping machinery, or alternatively by milling machinery such as a CNC milling machine. Alternatively, the initial device fabricated by this method may be in a temporary state for further consideration and or manipulation by the surgeon, and then finally constructed using one of the methodologies described herein. The steps may be repeated for complementary devices, some or all of which may include further matching surfaces for the patient's anatomy or to the previously fabricated devices (i.e., the devices fabricated may have matching surfaces for adjoining together one or more devices, as described in greater detail below).

Alternatively, the system and method described herein may facilitate the alignment of various anatomical features for a particular patient, such as, for example, multiple vertebral bodies in a patient to correct spinal deformities. For example, the data set(s) may provide an initial location for the anatomical features, but may be further manipulated by the surgeon in a pre-operative setting to create a desired data set(s), such as a final location for the anatomical features once the surgical procedure(s) are completed. In this manner, the devices formed by the system and method described above may be used in either an initial location or a final location for the anatomical features, and be matched to those specific locations and orientations for each stage of the surgical procedure. These staged devices would in turn provide the surgeon with a visual guide to determine the degree of correction achieved through the surgical procedure, as compared to the pre-operative plan. Other variations on the method of the present disclosure are described in the Summary of the Invention and included in the appended claims.

Fabrication methods may comprise the use of a rapid prototyping machine, such as a stereolithography (STL) machine, selective laser sintering (SLS) machine, or a fused deposition modeling (FDM) machine, direct metal laser sintering (DMLS), electron beam melting (EBM) machine, or other additive manufacturing machine. One example of such a rapid prototyping machine is commercially available from 3D Systems and known as Model SLA-250/50. The rapid prototyping machine selectively hardens a liquid, powdered or other non-hardened resin or metal into a three-dimensional structure, which can be separated from the remaining non-hardened resin, washed/sterilized and used directly as the apparatus. The prototyping machine receives the individual digital data sets and produces one structure corresponding to each of the desired apparatus.

Generally, because stereolithographic machinery produces a resin, which may have less than optimal mechanical properties (which may not be generally acceptable for a particular surgical use), the prototyping machine may alternatively be used to produce a mold. After the model is prepared, a conventional pressure or vacuum molding machine may be used to produce the apparatus from a more suitable material, such as stainless steel, titanium alloy, aluminum alloy, chromium alloy, PEEK, carbon fiber, or other metals or metal alloys.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

According to one particular embodiment of the present disclosure, a system and method is provided for fabricating apparatus for use with a variety of surgical procedures associated with a patient's spine. Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury.

For patients with varying degrees of degenerative disc disease and/or nerve compression with associated lower back pain, spinal fusion surgery, or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, thoracic or cervical spine region of a patient. Fusion requires tools for accessing the vertebrae and implanting the desired implant, any bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments. The insertion, alignment and placement of these tools, instruments and fixation devices are critical to the success of the operation. As such, providing a customized and patient-specific tool or instrument increases the likelihood that the surgical procedure will be successful.

Figure 3:
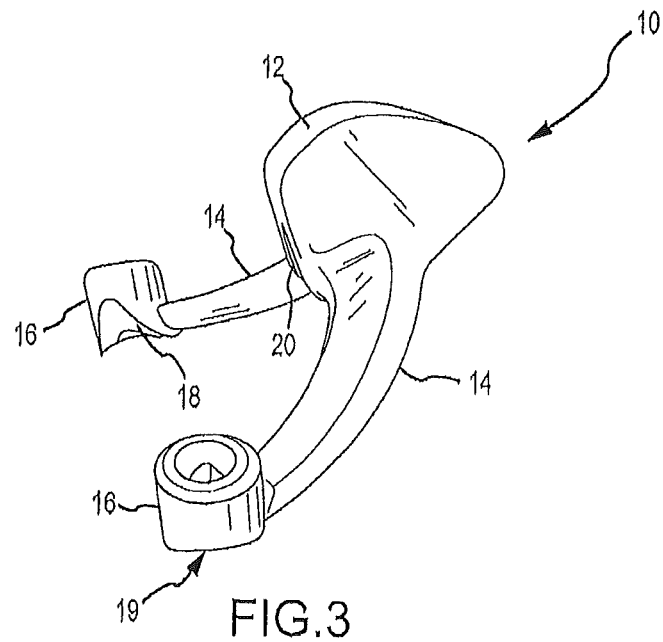
FIG. 3 is a side elevation view of a particular apparatus for facilitating a surgical procedure according to one embodiment of the present disclosure.
Figure 4:
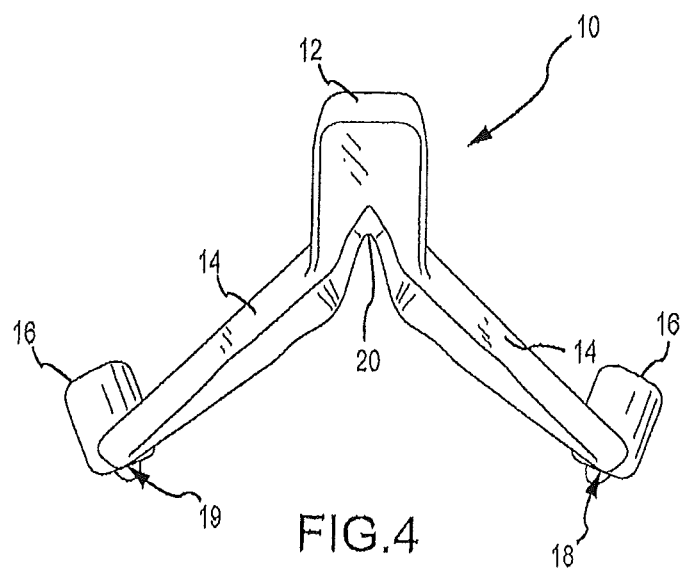
FIG. 4 is rear elevation view of the apparatus shown in FIG. 3.

For example, one particular apparatus formed by the system and method described above and that may be used for a particular fixation related surgery is depicted in FIGS. 3 and 4. According to one embodiment of the present disclosure, the apparatus may be in the form of a pedicle screw guide 10, which is comprised of a body 12 and two generally elongated wings 14, each wing 14 terminating in a column 16. In a preferred embodiment each of the columns 16 is substantially hollow to permit one or more types of devices to be inserted therethrough, as depicted in FIG. 3. The body 12 may further comprises a longitudinal cavity 20 formed about a lower surface of the body 12 (shown from the perspective view taken in FIG. 3). Each of the columns 16 further comprise a lower, patient-contacting surface 18, 19, which in conjunction with the longitudinal cavity 20 provide a plurality of patient specific contours for matching with a plurality of anatomical features, as described in greater detail below.

The contours and locations of the lower, patient-contacting surfaces 18, 19 and the longitudinal cavity 20 are formed by use of data set(s) converted from a MRI or CT scan of the patient. The remainder of the pedicle screw guide 10 shown in FIGS. 3 and 4 may be formed to meet the surgeon's particular preferences. For example, the wings 14 need only be of sufficiently length to locate the two columns 16 in the location of the corresponding patient-matched anatomical features. The wings may take on other shapes, orientations, thicknesses, etc. without deviating from the novel aspects of this disclosure. Similarly, the body 12 need only be sized to accommodate the longitudinal cavity 20 and may comprise other extensions other than the wings 14 to aid in grasping or manipulating the pedicle screw guide 10 as desired.

Additionally, the wings 14 may be made from a semi-malleable or semi-rigid material to create at least a partial interference fit when the pedicle screw guide 10 is placed on the corresponding anatomical grouping for the particular surgery. For example, a snap or interference fit may be formed by subtle deflection of the wings 14 when placing the two columns 16 adjacent the inferior articular process, and then deflect to the desired location once the wings are positioned in their final orientation. Further aspects of the disclosure in this respect are described in greater detail below.

Figure 5:
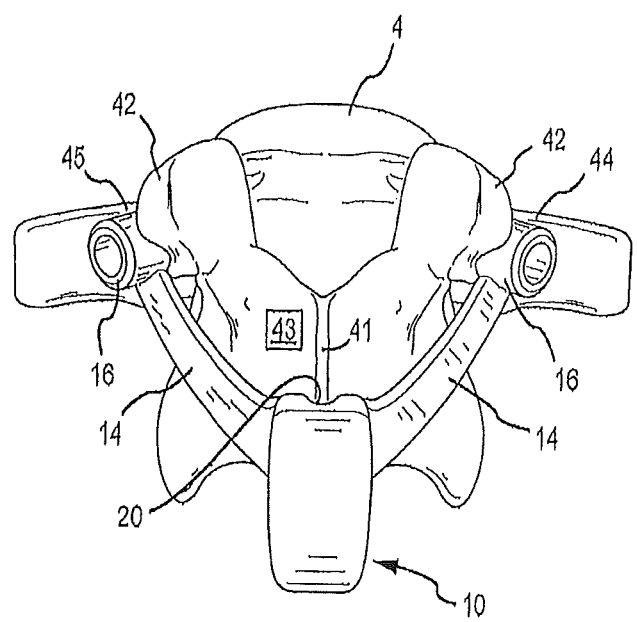
FIG. 5 is a top plan view of the apparatus shown in FIG. 3, relative to a unique grouping of anatomical features, and according to one embodiment of the present disclosure.

FIG. 5 is a plan view of the apparatus shown in FIG. 3 relative to a unique grouping of anatomical features according to one embodiment of the present disclosure. Here, the pedicle screw guide 10 is positioned so that the body 12 is centrally located above the central portion of a vertebral body 4, such that the longitudinal cavity 20 mates with the contours of the spinous process 41 for this particular vertebral body 4. Similarly, the columns 16 are positioned one at each medial side of the pedicle screw guide 10 so that the wings 14 span the lamina 43 of the vertebral body 4 and the columns 16 are located proximate to the inferior articular process 44, 45. The lower, patient-contacting surface 18, 19 of columns 16 are formed to mate with the contours of the inferior articular process 44, 45 and behind the superior articular process 42.

Thus, the pedicle screw guide 10 provides a plurality of mating or matching locations, any one of which, if not positioned correctly, will impact the seating of the other two. In this aspect the pedicle screw guide provides a notable improvement over the prior art, which may be slightly rotated, misaligned or misplaced and still appear to the surgeon as if the device is properly seated. The redundancy and plurality of mating surfaces ensures that the pedicle screw guide 10 is both properly located and properly aligned. If the pedicle screw guide 10 is not properly located or aligned, the lower, patient-contacting surfaces 18, 19 will not fit on each of the inferior articular processes 44, 45 and thereby prevent the longitudinal cavity 20 from being firmly seated on the spinous process 41.

Figure 6:
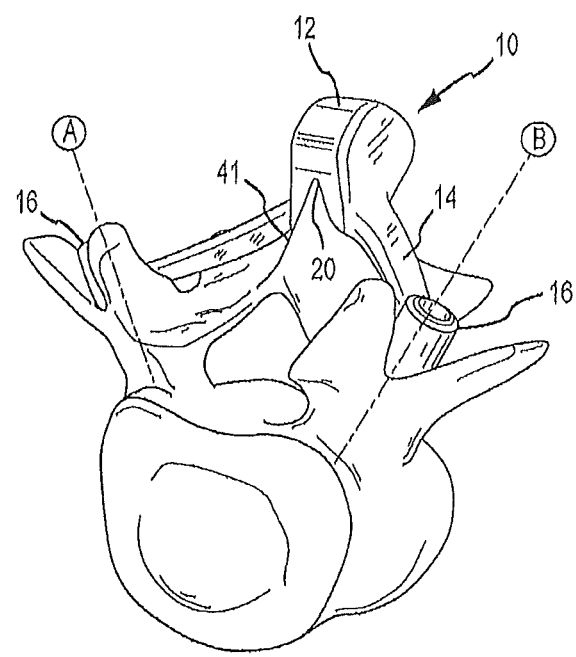
FIG. 6 is a perspective view of the apparatus and unique grouping of anatomical features shown in FIG. 5.

FIG. 6 is a perspective view of the apparatus shown in FIG. 5. Desired insertion trajectory lines A, B are shown to demonstrate that the locating of the columns 16 is in addition to the orientation of the axes for each of the columns 16, which may be independent relative to their seating adjacent the inferior articular process 44, 45 (i.e., the direction of the axis relative to normal may be different among the columns 16). The orientation of the columns 16 is preferably derived from the data set(s) described above, and in one preferred embodiment is selected based on the orientation that will permit a fixation device (i.e., pedicle screw) to be inserted consistent with the location of the pedicle and in a direction that avoids penetration of the fixation device from the pedicle (i.e., eliminates the possibility of the screw either extending through the pedicle or becoming inserted at an angle that causes the pedicle screw to exit the side of the pedicle).

Figure 7:
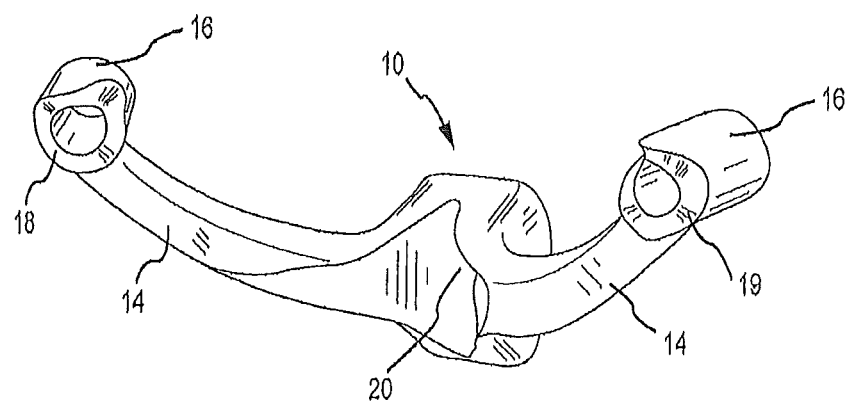
FIG. 7 is another perspective view of the apparatus shown in FIG. 3 demonstrating the customized patient-matching surfaces of the apparatus.

The customized or configured patient-contacting surfaces of the apparatus shown in FIGS. 3-6 are demonstrated by the bottom perspective view of the pedicle screw guide 10 in FIG. 7. Here, the lower, patient-contacting surfaces 18, 19 may comprise dynamic contours having multiple compound radii, such that the surfaces 18, 19 are completely congruent with the corresponding anatomical features of the vertebrae. Thus, the surfaces conform substantially to the surface of the vertebrae where the columns 16 are to be located during the surgical procedure, and would not conform substantially to a different surface of the vertebrae. In this manner, the surgeon is informed immediately if the pedicle screw guide 10 is misaligned, because it will not properly seat on the vertebrae.

Figure 8:
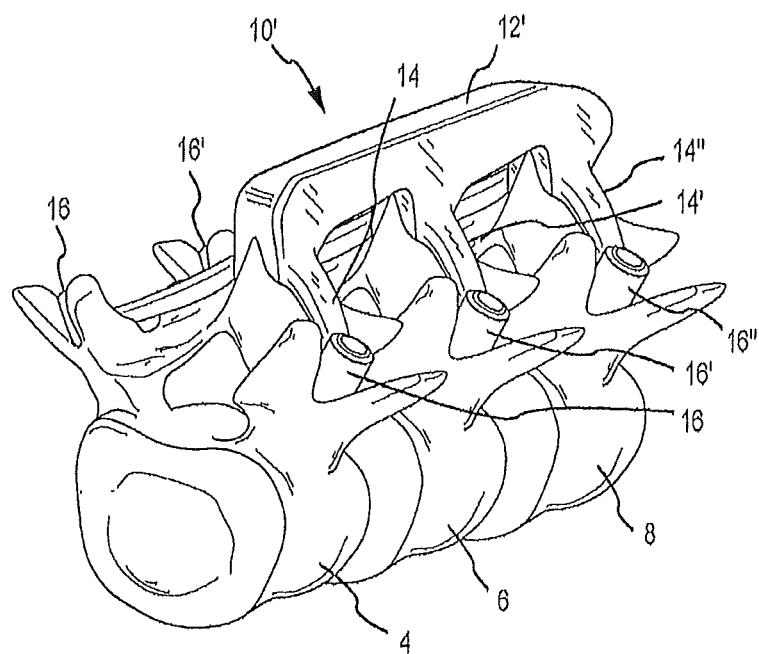
FIG. 8 is a perspective view of an apparatus according to an alternative embodiment of the present disclosure.

FIG. 8 shows an apparatus according to an alternative embodiment of the present disclosure. In this embodiment, a multi-level pedicle screw guide 10' is shown relative to several adjoining vertebral bodies 4, 6, 8. The multi-level pedicle screw guide 10' comprises multiple secondary wings 14' and tertiary wings 14", which each have corresponding columns 16', 16" for inserting and aligning a plurality of pedicle screws into the adjoining vertebral sections 6, 8. It is expressly understood that multiple levels in number greater than or less than three may be achieved without departing from the spirit of the present invention.

Figure 9:
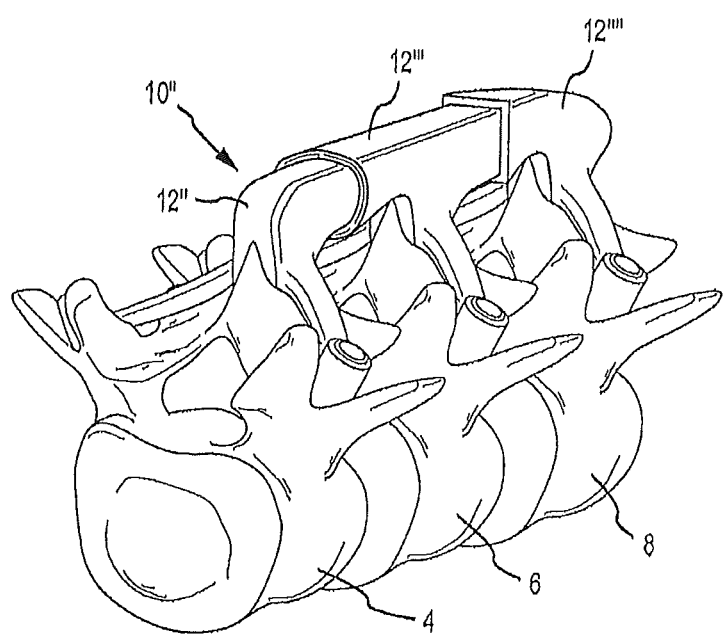
FIG. 9 is a perspective view of an apparatus according to yet another alternative embodiment of the present disclosure.

FIG. 9 shows an apparatus according to yet another alternative embodiment of the present disclosure, which is comprised of multiple sections 12", 12''', 12''''. Similar to the embodiment shown in FIG. 8, this pedicle screw guide 10" permits alignment and insertion of pedicle screws in multiple levels 4, 6, 8 of the spine. However, the multiple sections 12", 12''', 12'''' each have a modified body that comprises an engaging end and a receiving end, such that the multiple sections 12", 12''', 12'''' may be joined as shown in FIG. 9. The receiving and engaging ends of each of the multiple sections 12", 12''', 12'''' are different so that when assembled, only the proper ordering of the sections 12", 12''', 12'''' may be achieved (i.e., section 12" may only be joined with section 12'''). This figure demonstrates yet another aspect of the present disclosure, in particular, the ability to mate or join specific devices adjacent to one another to further ensure alignment and mating with the particular anatomical features associated with each device, as well as provide a means for applying corrective force to the vertebrae and visualize the degree of deformity correction.

Figure 10:
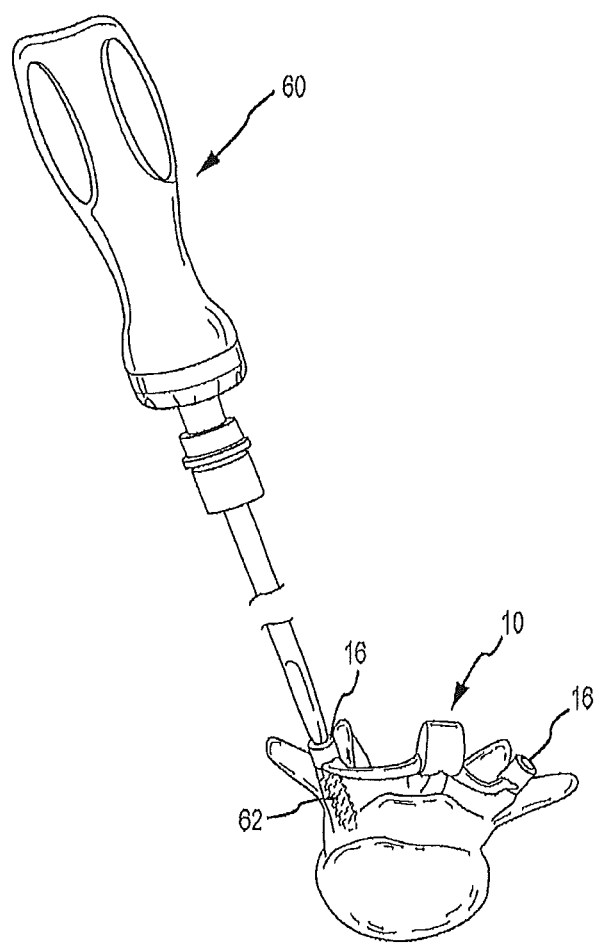
FIG. 10 is another perspective view of the apparatus shown in FIG. 3 along with a custom fabricated instrument for use during a particular surgical procedure.

FIG. 10 shows an apparatus according to the embodiment of FIG. 5 with a customized instrument, which may be used in concert with the apparatus during a particular surgical procedure. For example, during a spinal fusion procedure such as the one described above, it is common for the surgeon to attach one or more pedicle screws to the vertebrae of the patient to achieve the desired fusion of intra-vertebral bodies. The column 16 may have an internal diameter that corresponds with a gradually increasing external diameter of the instrument 60 such that the instrument 60 may only be advanced into the column 16 to a predetermined distance, thereby providing a hard stop and in turn providing means for preventing the pedicle screw 62 from advancing too far into the boney anatomy of the patient. According to yet another embodiment, the hollow portion of the column 16 may have a section with a narrower internal diameter (not shown in FIG. 10), which corresponds to a end-stop fitted to the external diameter of the instrument 60 in a manner and location to prevent the instrument from over penetrating the column 16 and thereby inserting the pedicle screw 62 beyond a safe limit.

Figure 11A:
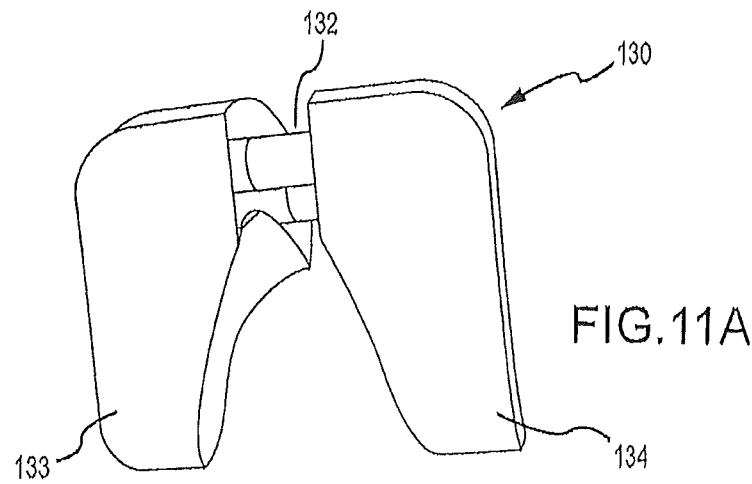
FIGS. 11A-B are perspective views of an apparatus according to another alternative embodiment of the present disclosure.
Figure 11B:
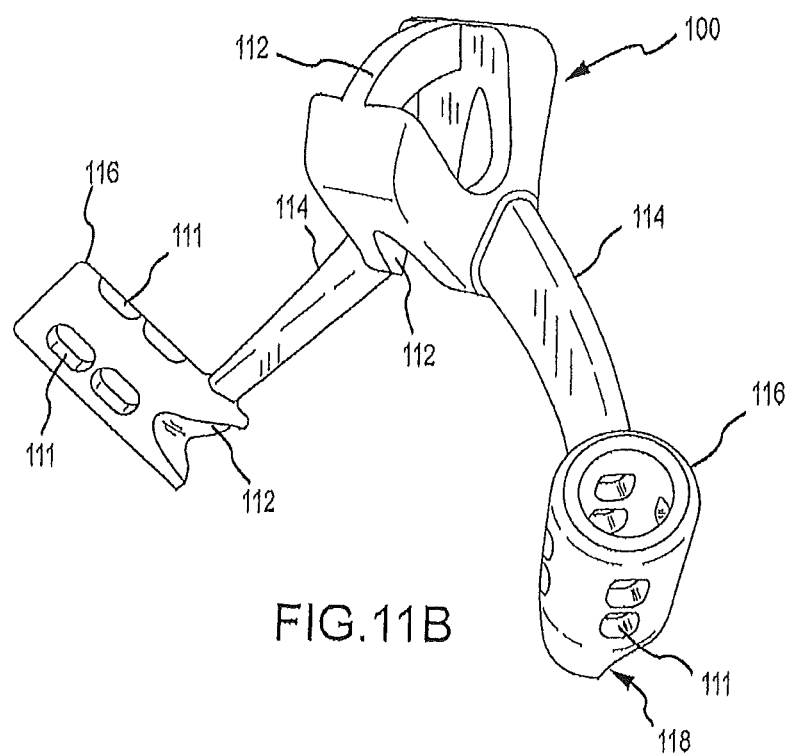
Figure 12:
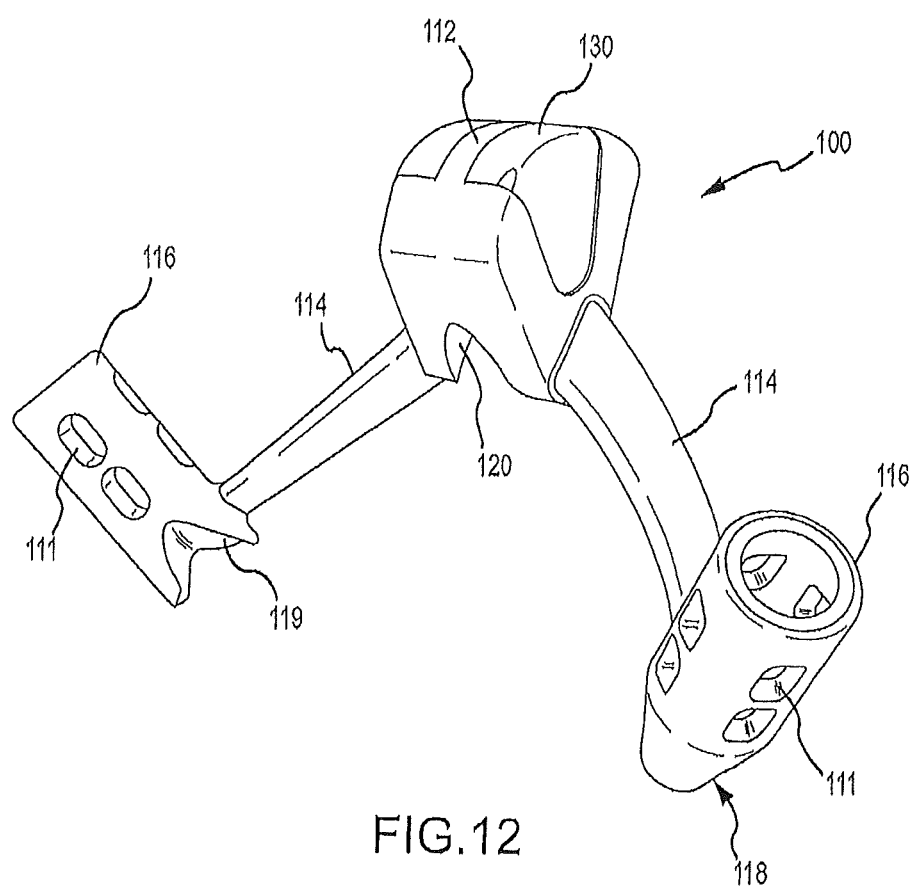
FIG. 12 is a perspective view of the apparatus shown in FIGS. 11A-B in an assembled state.

FIG. 11 is a perspective view of an apparatus according to yet another alternative embodiment of the present disclosure. Here, the apparatus is a pedicle screw guide 100 which further comprises a narrow bridge 112 about the body, which permits a collar 130 to be coupled with the modified pedicle screw guide 100, as shown in FIG. 12. The collar 130 may comprise a contoured lower surface matching the spinous process of the patient (similar to the longitudinal cavity of the embodiment shown in FIG. 3) and may be inserted into the pedicle screw guide 100 for matching the particular anatomical feature for the vertebrae operated on during the surgery. Thus, in this embodiment, the collar 130, in addition to the lower patient-contacting surfaces 118, 119 of the two columns 116, comprises at least one of the patient-matching contours, and may be removed and replaced with other collars of differing contour as required for surgical procedures on different vertebrae. In this embodiment, the columns 116 may further comprise one or more apertures 111 to facilitate visualization of the pedicle screw while it is being advanced into the columns 116.

Figure 13:
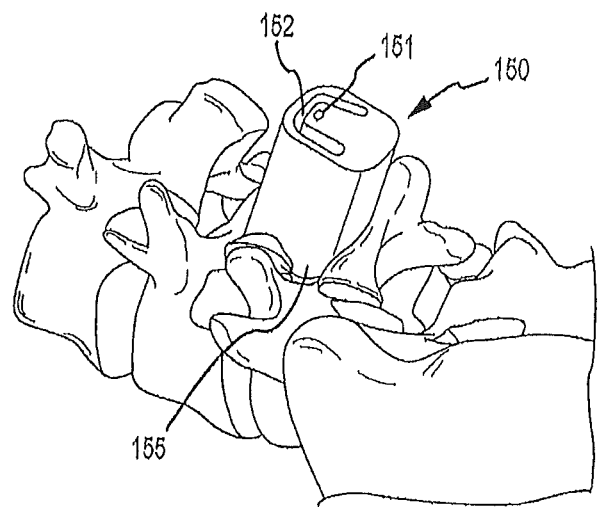
FIG. 13 is a perspective view of an apparatus according to yet another alternative embodiment of the present disclosure.

FIG. 13 is a perspective view of an apparatus for facilitating a surgical procedure according to yet another alternative embodiment of the present disclosure. In this embodiment, the apparatus formed by the system and method described above is comprised of a laminectomy cutting guide 150. This laminectomy cutting guide further comprises at least one alignment channel 151 for inserting a guide wire or other securing element, and a cutting slot 152 for directing the path of a blade or other cutting edge. As with the pedicle screw guide described in FIG. 3 above, this laminectomy cutting guide 150 also comprises a lower patient-contacting surface 155 which permits the laminectomy cutting guide 150 to mate with one or more vertebral bodies. Although shown in FIG. 13 as a generally rectangular prism, it is expressly understood that other geometrical shapes for the laminectomy cutting guide 150 are equally as practical, and considered within the scope of the disclosure.

Figure 14:
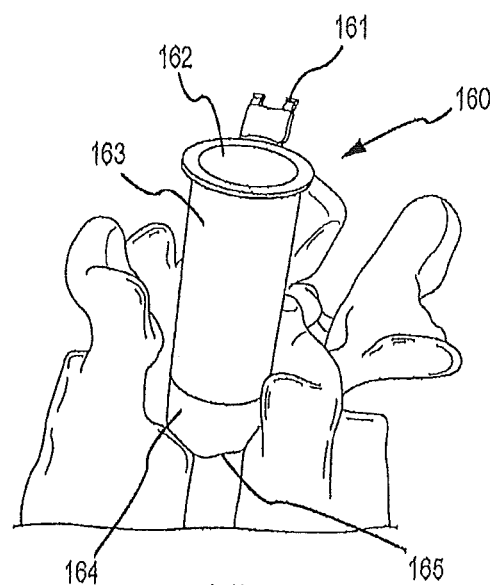
FIG. 14 is a perspective view of an apparatus according to yet another alternative embodiment of the present disclosure.

FIG. 14 shows yet another alternative embodiment of the present disclosure. In this embodiment the apparatus formed by the system and method described above is comprised of a tube retractor 160, which also comprises a lower patient-contacting surface 165. This patient-contacting surface 165 may be formed in a section 164 of the tube retractor that is selectively removable from the body 163 of the tube retractor 165, such that the tube retractor 165 may be reused in a number of surgeries while the section 164 is reformed and coupled to the body 163 for each patient. The tube retractor also comprises a generally hollow inner lumen 162 and at least one tab 161 for manipulating during insertion and that assists the surgeon in ensuring proper alignment of the tube retractor 160.

Figure 15:
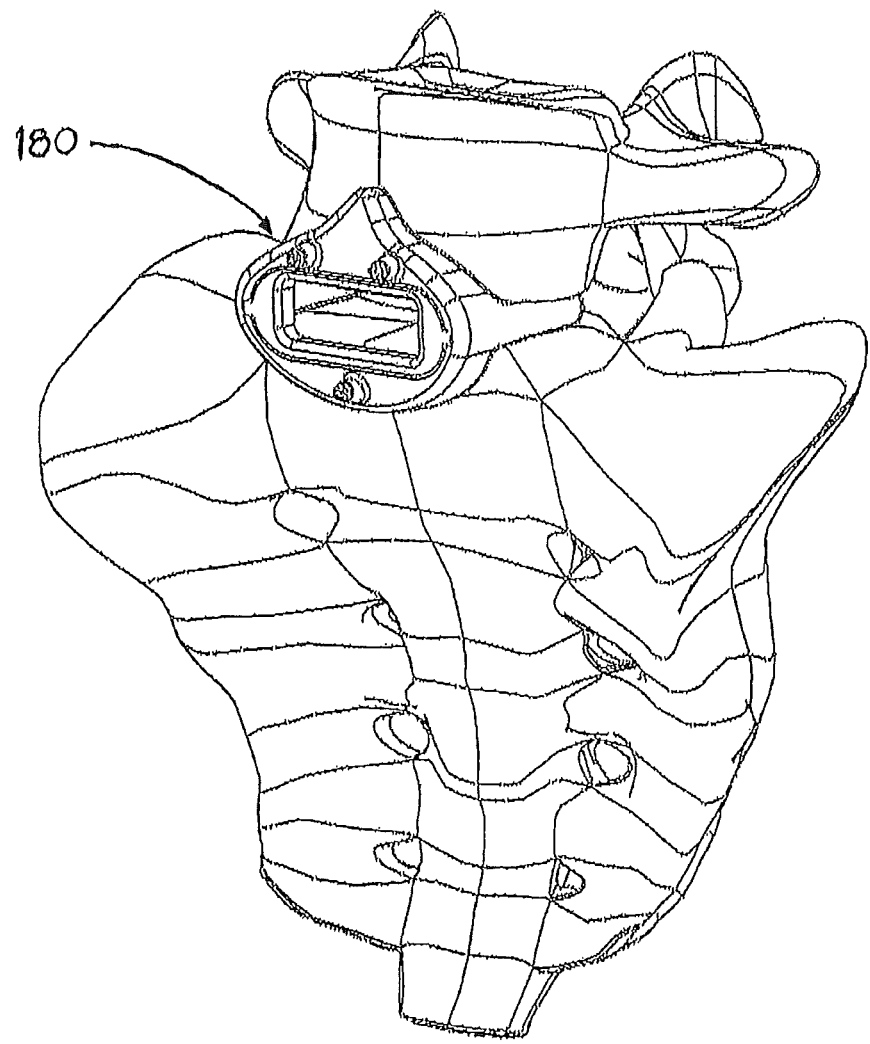
FIG. 15 is a perspective view according to yet another alternative embodiment of the present disclosure.
Figure 16:
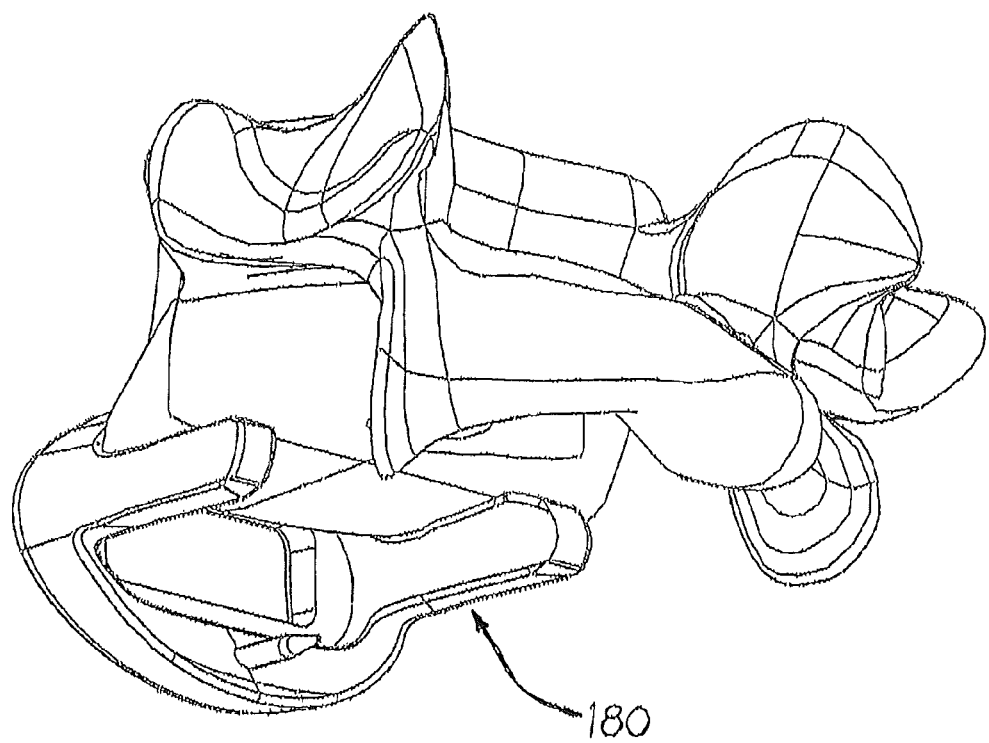
FIG. 16 is a different perspective view of the apparatus shown in FIG. 15.
Figure 17:
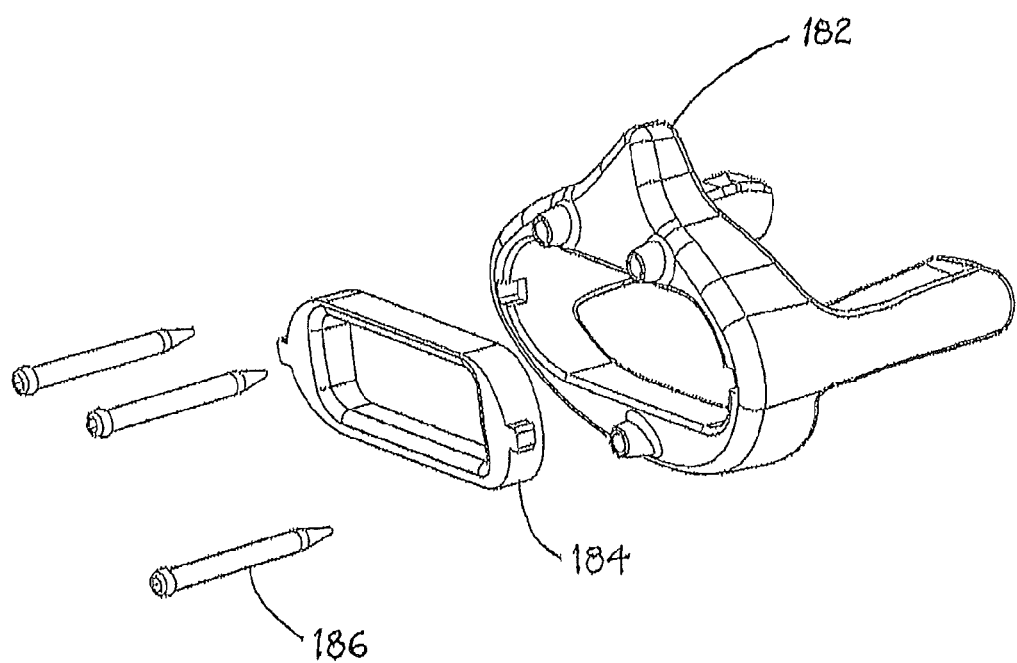
FIG. 17 is an exploded perspective view of the apparatus shown in FIG. 15.

FIGS. 15-17 demonstrate yet another alternative embodiment of the present disclosure. In this embodiment, the template may comprise a patient-matched guide 180 for facilitating the placement of one or more interbody devices, such as by way of example but not limitation, an implantable cage for introducing one or more bioactive substances or bone graft, or an artificial disc. In FIGS. 15 and 16, the patient-matched guide 180 is shown in one potential location relative to a unique anatomical grouping (between two adjacent vertebrae) for assisting the surgeon for placing one or more interbody devices.

In FIG. 17, the patient-matched guide 180 is shown in an exploded view to demonstrate how a plurality of components may be fabricated using the system and method described above for a particular surgical procedure. These components include a patient-specific insert 182, a guide sleeve 184 and connectors 186, which in a finally assembled state form the patient-matched guide 180 shown in FIG. 15.

Referring now in detail to FIGS. 18-19, another alternative embodiment of the present disclosure is shown. According to this embodiment, a surgical template 190 is depicted, which may further incorporate a plurality of fixation devices 198, 198', which may be used to secure the template 190 in a variety of different ways. According to this embodiment, the template 190 comprises an intermediate section 192 oriented to bridge a patient's spinous process, and may further comprise apertures (not shown in FIGS. 18-19) for inserting one or more fixation devices 198, 198'. The template 190 may further comprise two laterally extending portions or "wings" 194 which each terminate with a guide 196. The description of the guides provided above in connection with other embodiments disclosed herein is hereby incorporated by reference with respect to this embodiment.

According to the embodiment shown in FIGS. 18-19, fixation devices 198, 198' may be inserted through apertures (not shown) in the intermediate section 192 of the template 190 for stabilizing and securing the template 190 to the patient's spinous process. According to one embodiment, the direction and orientation of a first fixation device 198 is different than the orientation and direction of a second fixation device 198' to further improve the stability of the template 190 prior to insertion and placement of the permanent fixation devices. According to yet another embodiment, the apertures may be located in different locations than depicted in FIGS. 18-19, and may be fewer or greater in number according to the demands of the surgery and the patient's specific boney anatomy.

Figure 20:
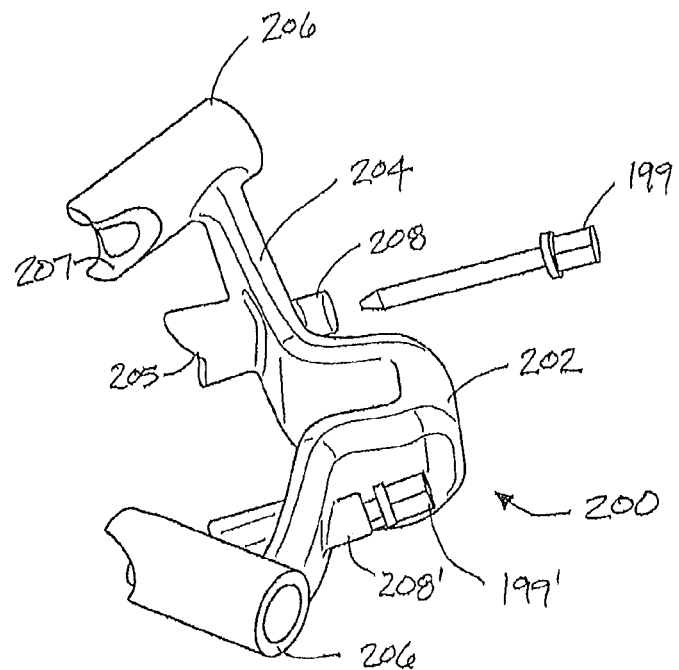
FIGS. 20-21 are perspective views according to yet another alternative embodiment of the present disclosure.
Figure 21:
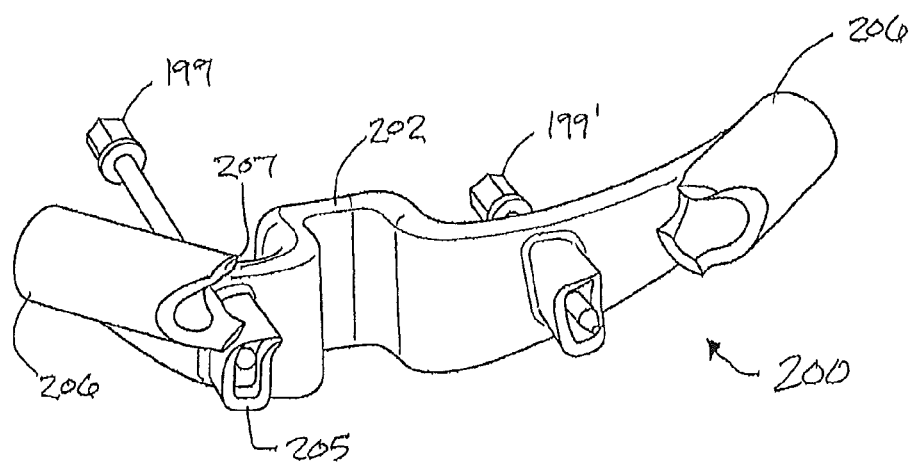

Referring now in detail to FIGS. 20-21, yet another alternative embodiment of the present disclosure is shown. In this embodiment, the template 200 further comprises two additional contacting surfaces 205 which preferably have a hollow opening at the patient-contacting end and an aperture extending therethrough for inserting a fixation device 199, 199'. As described above in connection with FIGS. 18-19, the purpose of the fixation devices 199, 199' is for securing the template 200 to the boney anatomy and facilitate securing permanent fixation devices (not shown) through a plurality of guides 206.

Referring to FIG. 20, the template 200 includes a boss 208 extending from a top surface of the template 200 for inserting a first fixation device 199, wherein the boss 208 is partially hollow to accommodate the shape and length of the fixation device 199. The boss 208 extends above a laterally extending portion or "wing" 204 of the template 200 as shown in FIG. 20. The boss 208 may extend more or less above the template than shown in FIG. 20 to provide a hard stop against over insertion of fixation device 199. Similarly, the opposite laterally extending portion or "wing" of the template 200 also comprises a boss 208' for inserting a second fixation device 199'.

Incorporating the disclosure above with respect to determining and modeling patient contacting surfaces, according to this embodiment the template 200 has at least four patient specific contacting surfaces 205, 207. This embodiment improves stability and positioning of the template, and allows a surgeon to achieve a dynamically stable surgical template, which in turn ensures that all permanent fixation devices are being positioned and inserted in a direction and orientation pre-determined for the particular surgical demands. This is accomplished by providing the four patient contacting surfaces, which act like independent legs of a table, and being positioned at different locations (and at different planes) with respect to the patient's boney anatomy to further improve the stability and positioning of the template 200.

According to the embodiment shown in FIGS. 18-21, the guides and other patient contacting surfaces may be depth-specific, and may further incorporate specific internal diameters to accommodate insertion of a temporary fixation device to a controlled depth within the patient's boney anatomy. Furthermore, the guides may have specific threaded internal surfaces to accommodate a specific fixation device and to facilitate insertion of a threaded fixation device, such as a screw. In certain embodiments, the templates could be designed for a specific patient to prevent excessive penetration of the fixation devices into the boney anatomy, or facilitate a depth-controlled first set of fixation devices to temporarily secure the templates.

According to yet another embodiment, each of the patient contacting surfaces may have an integrated blade with a patient-contacting cutting surface, integrated about at least a portion of the patient contacting surface to further set and secure the template to the boney anatomy prior to insertion of the fixation devices. The purpose of the blade is to cut through the soft tissue to achieve better template to bone contact between the template and the patient's boney anatomy. The hollow portions of the guides and other patient contacting surfaces of the template further permit soft tissue to become positioned within these hollow surfaces after the template has been set in the desired location, further securing the template to the patient's boney anatomy. The blade may be substantially cylindrical or ring shaped to match the shape of the guide, or may be oval, polygon, or other shape to match a patient contacting surface.

To add further stability to the seating and placement of the patient contacting surfaces described herein to the patient anatomy, the contacting surfaces may further comprise one or more spikes or teeth, which serve to contact and at least partially penetrate the patient anatomy to secure the device in place. In one embodiment, the spikes or teeth may be made of the same material and may be permanently attached to the patient contacting surfaces. In another embodiment, the spikes or teeth may be made of a different material, such as the ones described herein, and may further be selectively inserted onto one or more of the patient contacting surfaces as desired.

Figure 22:
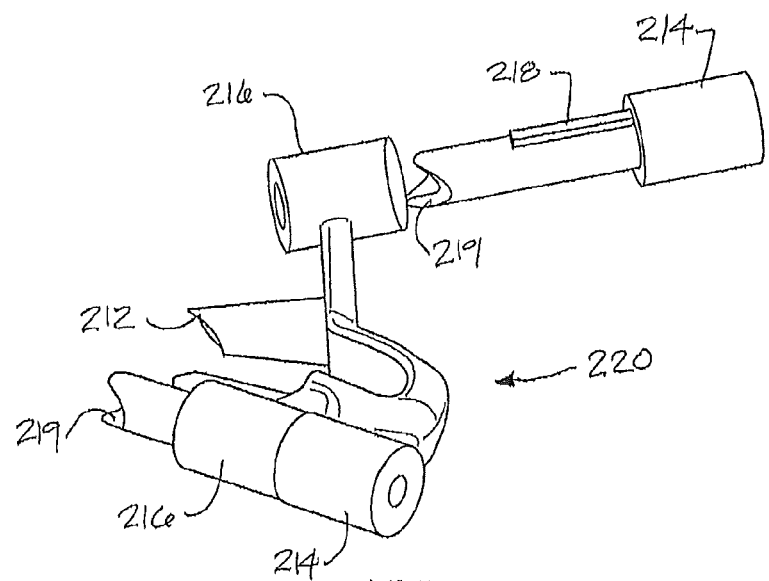
FIG. 22 is a perspective view according to yet another alternative embodiment of the present disclosure.

Referring now to FIG. 22, yet another alternative embodiment of the present disclosure is shown. According to this embodiment, the template 220 has a plurality of patient contacting surfaces 212, 219, which are achieved through the use of a "floating" patient-matched component 214, which may inserted into one of a plurality of guides 216 either before or after the first set of patient contacting surfaces 212 are positioned. The patient-matched component 214 may further comprise a longitudinal key 218 which corresponds to a slot or groove (not shown in FIG. 22) in the guide 216 for facilitating proper location (rotationally) of the patient-matched component 214 respective of the template 220.

Thus, according to this embodiment, the template 220 may be secured in a first position by using at least two fixation devices (not shown) securing the template 220 to its desired location, and then a plurality of patient-matched components 214 may be inserted into the guides 216 of the template 220 and seated about two distinct locations of the patient's boney anatomy.

Figure 23:
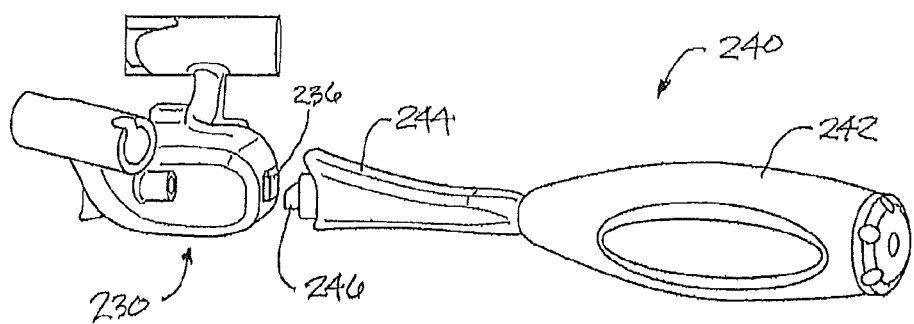
FIG. 23 is a perspective view according to yet another alternative embodiment of the present disclosure.

Referring now to FIG. 23, yet another embodiment of the present disclosure is shown, wherein a instrument 240 may be used to facilitate insertion of a template 230 according to various embodiments disclosed herein. The instrument 240 is preferably comprised of a handle 242 and an extending arm 244, the length of which may vary depending on the specific patient's anatomical features and/or surgeon preferences. At the distal end of the extending arm 244 is a tab 246, which is formed to match a corresponding slot 236 located on one surface of the template 230. In operation, the instrument 240 may be joined with the template 230 and used to insert and position the template 230 within the patient's surgical site.

Figure 24:
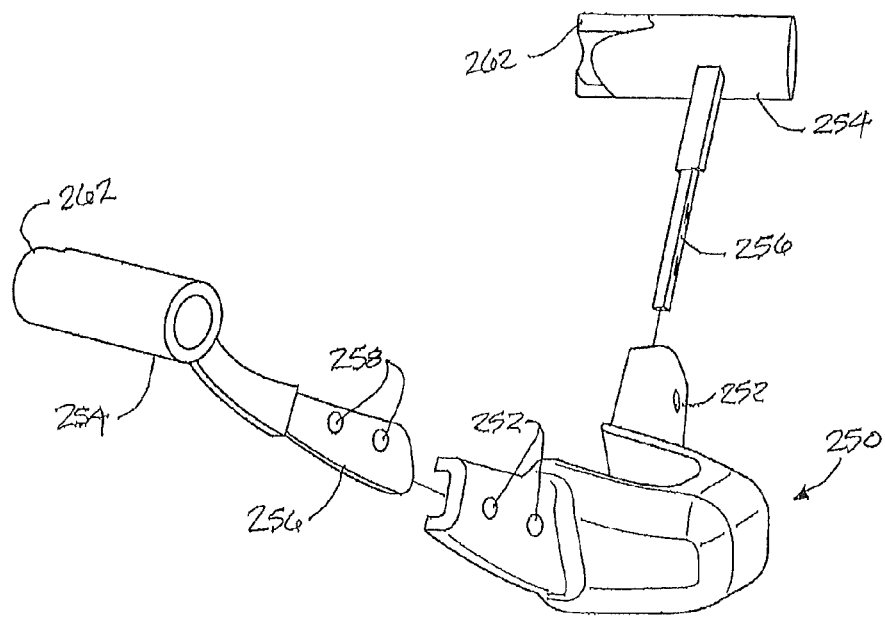
FIG. 24 is a perspective view according to yet another alternative embodiment of the present disclosure.

Referring now to FIG. 24, another alternative embodiment of the present disclosure is shown. According to this embodiment, a template 250 may be provided which is not patient specific (but in an alternate embodiment, may be patient specific) and further provides means of attaching a plurality of patient specific components 254 to the template 250. As shown in FIG. 24, the components 254 may be secured to the template 250 by aligning apertures 252, 258 and attaching one or more securing devices (not shown in FIG. 24) such as a screw, pin, or other like device. Once the components 254 are secured to the template 250, the patient contacting surfaces 262 may be used to guide and position the template 250 with the integrated components 254 in the desired location. In this manner, a standard template 250 may be provided prior to obtaining any patient data, and combined with patient specific components 254 that are formed after the patient anatomical data has been captured, thereby eliminating custom machining or fabrication of the template for a specific surgical application.

According to this embodiment the template 250 may be reusable, or in an alternative embodiment may be disposable. The template 250 may be comprised of any of the materials listed herein, but in a preferred embodiment is formed of a metal, metal alloy or a polymeric-based material. According to yet another alternative embodiment, the components 254 may snap into place or have a friction-fit connection and therefore do not require screws or other securing devices to attach to the template 250. In yet another alternative embodiment, the template 250 may be provided in a variety of set sizes and orientations to cover variability in patient anatomy and different size vertebral bodies (with respect to different levels or regions of the patient's spine).

Figure 25:
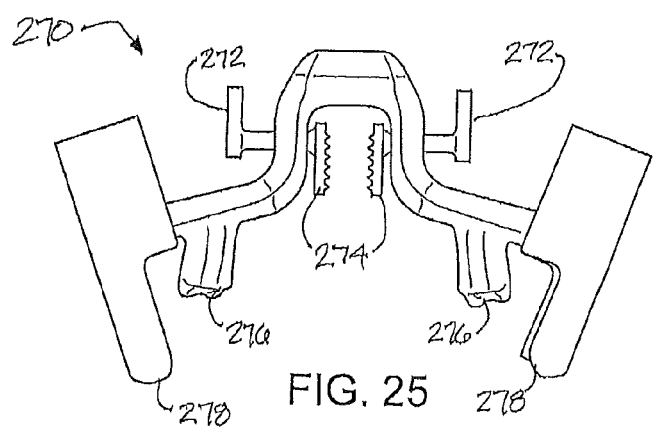
FIG. 25 is a perspective view according to yet another alternative embodiment of the present disclosure.

Referring now in detail to FIG. 25, another embodiment of the present disclosure is shown. In this embodiment, the template 270 has a plurality of patient contacting surfaces 276, 278 and further comprises a plurality of clamps 272 for securing the template 270 to the Spinous Process of the patient. According to this embodiment, the clamps 272 each have a patient contacting surface 274 (here designed to contact the spinous process about each lateral side) to secure the template to the desired location of the patient's anatomy. Each of the clamps 272 may be positioned laterally with respect to the template 270 (shown in an elevation view) and affixed to a set position with respect to the body of the template 270. The clamps 272 may be secured in a fixed position against the spinous process by a number of known means, including a latch mechanism, a ratcheting mechanism, a direction-specific resistance mechanism, or a selectively-releasable tightening mechanism. In this embodiment, the clamps 272 allow oppositional forces occurring in the boney anatomy to become balanced relative to the patient's template 270. In turn, the clamping mechanism ensures and maintains the alignment of the template 270 relative to the boney surfaces further ensuring accuracy with respect to insertion of permanent fixation devices. The clamps can take a variety of shapes or embodiments including pins, paddles, or any other type of opposing surfaces that apply juxtapositional stabilizing forces.

According to one embodiment, the surgical guides depicted in FIGS. 24 and 25 may include surfaces about the patient contacting end of the guide sleeves (see 254, FIG. 24) to conform to the soft tissue existing at the facet complex where the patient contacting end of the guide sleeve contacts the patient's vertebrae (see 278, FIG. 25). Thus, according to this embodiment, the guide sleeve(s) comprise a patient contacting surface that resembles a half cylinder or partial cylinder (as shown in FIGS. 24 and 25) to avoid contact with this soft tissue.

Figures 26A, 26B:
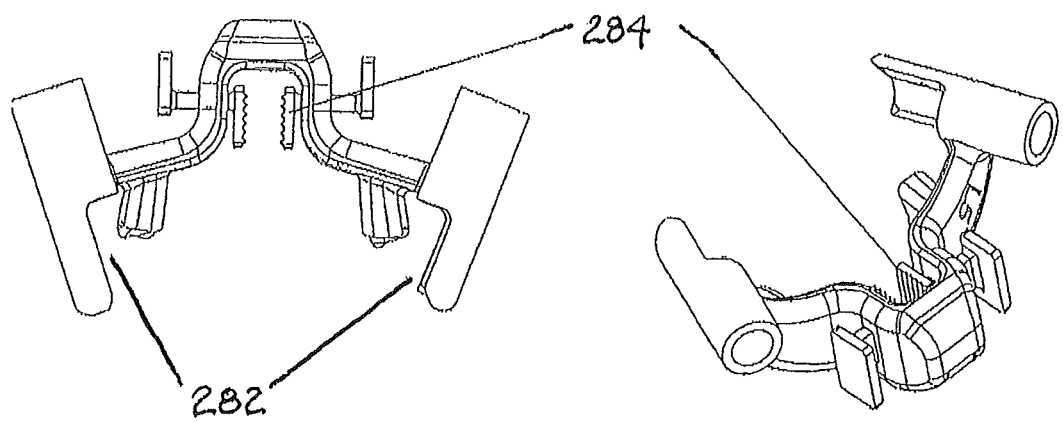
FIG. 26A is a perspective view according to yet another alternative embodiment of the present disclosure.
FIG. 26B is a perspective view according to the embodiment shown in FIG. 26A.

In one alternate embodiment, the surgical guide may further comprise one or more portions that have been cut-out or may selectively be cut-out or broken off to facilitate placement. One such surgical guide is shown in FIGS. 26A and 26B. According to this embodiment, the surgical guide comprises a plurality of patient contacting surfaces, one or more of which has been modified to facilitate clearance of the guide as it is being placed into position (see surfaces 282 on FIG. 26A). Furthermore, a surgical guide as described herein may comprise one or more clamping elements for securing the guide in a preferred location, such as the clamp 284 depicted in FIGS. 26A and 26B.

Figures 27A, 27B:
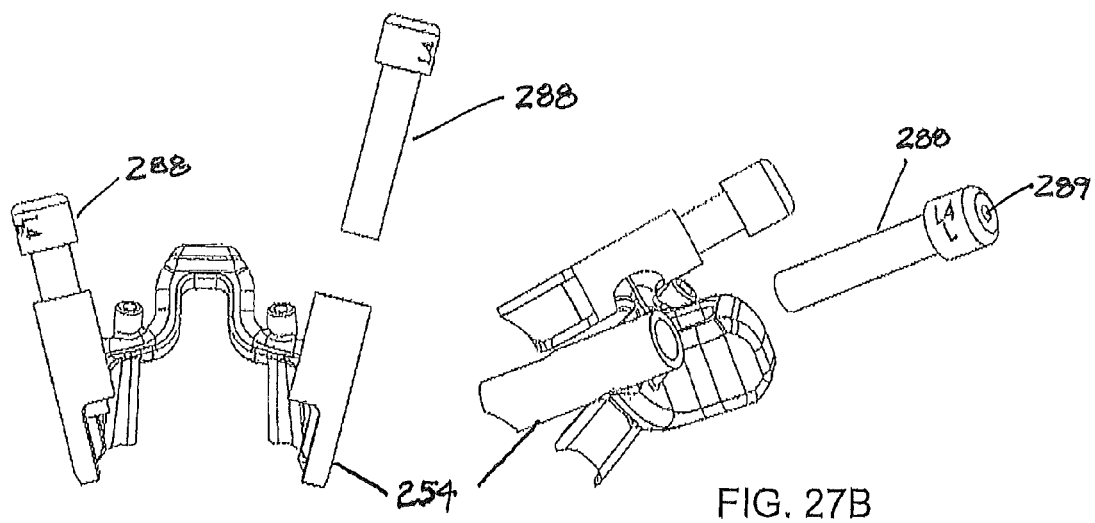
FIG. 27A is a front elevation view according to yet another alternative embodiment of the present disclosure.
FIG. 27B is a perspective view according to the embodiment shown in FIG. 27A.

According to yet another embodiment, the guide sleeve(s) 254 may further permit insertion of one or more inserts 288, as shown in FIGS. 27A and 27B. These inserts 288 may be sized with external diameters for mating with the interior diameter of the guide sleeve(s) 254, and have an interior aperture running longitudinally through the insert 288 for accommodating a drill bit or tap (by way of example) of varying sizes. In practice, the insert 288 may facilitate and guide a drill bit for creating a pilot hole for further insertion of a fixation device, such as a screw. According to one embodiment, inserts 288 may further comprise one or more indicia for identifying the specific insert 288 for a particular level of a patient's spine, or other indicia indicating the direction, orientation, use or purpose of said insert 288.

Figure 28:
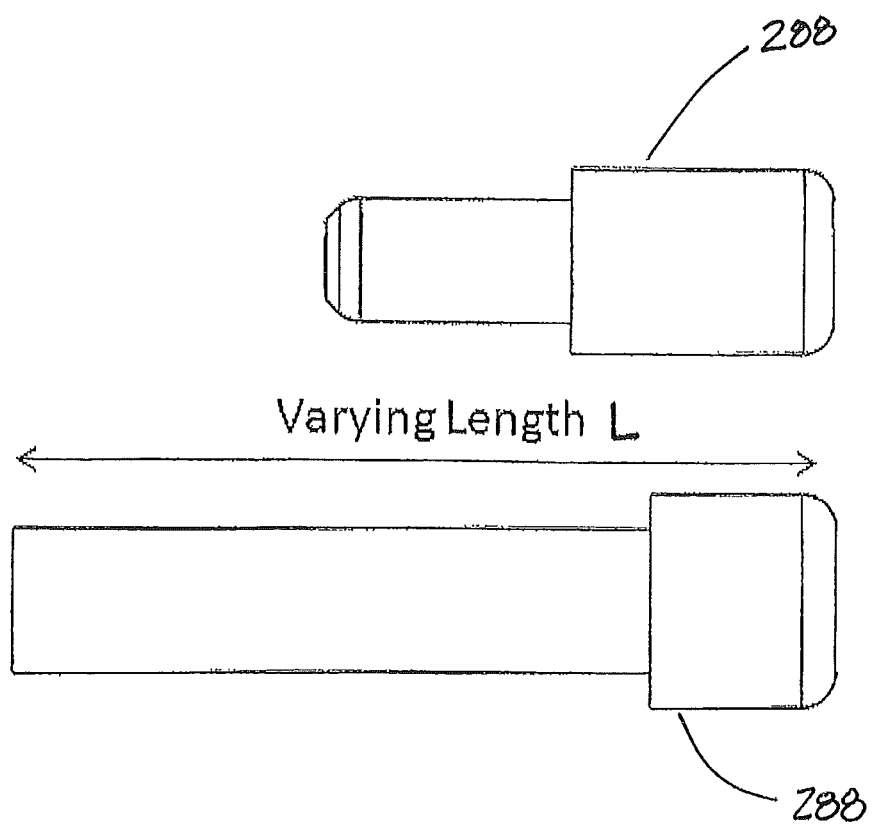
FIG. 28 is an elevation view according to yet another alternative embodiment of the present disclosure.
Figure 29A:
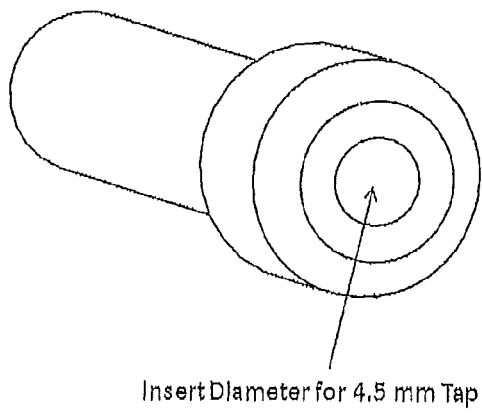
FIG. 29A is a perspective view according to yet another alternative embodiment of the present disclosure.
Figure 29B:
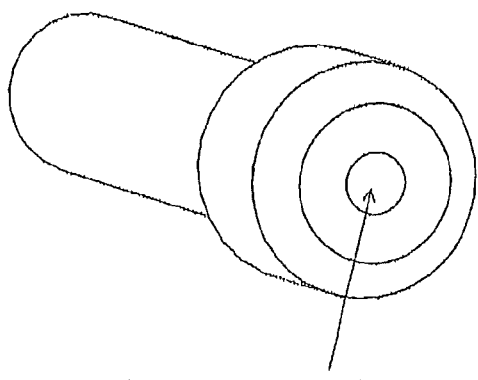
FIG. 29B is a perspective view according to yet another alternative embodiment of the present disclosure.

Referring now to FIG. 28, the inserts 288 provided with the surgical guides for mating with the guide sleeves 254 may have a varying length L, and may be made longer or shorter depending on the geometry of the guides, the patient's anatomy, the purpose of the insert, etc. For example, if a greater depth of a particular drill is required, the insert 288 may be shorter to accommodate further penetration of the drill bit into the patient's vertebrae. Likewise, the interior aperture of the insert 288 may have varying diameter depending on the precise tool or instrument that is intended to be used with the insert (as depicted in FIGS. 29A and 29B). In this manner, a surgeon may insure that he or she is using the proper tool, such as a drill or tap, with each of the inserts (which may further include one or more indicia to indicate the location or specific use intended for said insert) when performing a surgical procedure. Further illustration of the principles described above see FIGS. 29A and 29B, which depict an insert with a 4.5 millimeter aperture diameter for placement of a tap instrument and a ⅛ inch aperture diameter for use in connection with a ⅛ inch drill bit, respectively.

Figure 30:
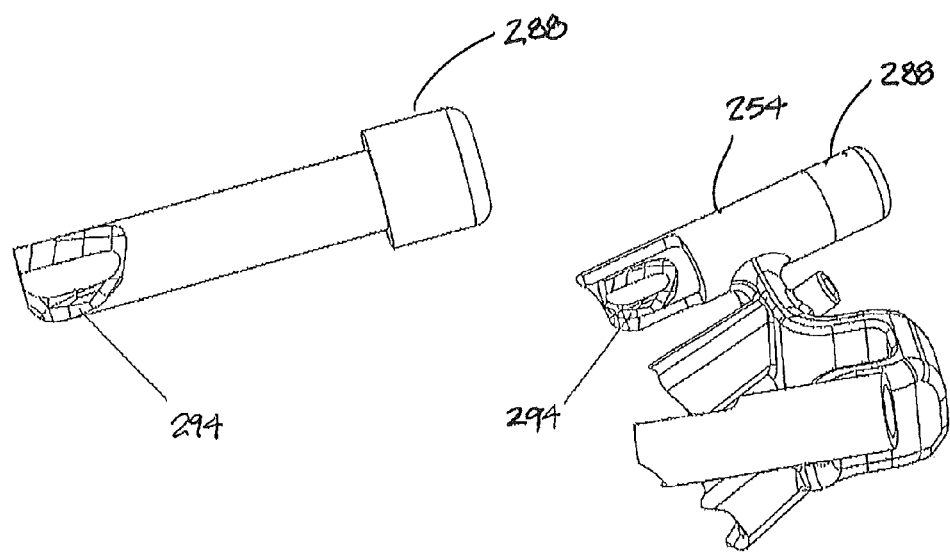
FIG. 30 is a perspective view according to yet another alternative embodiment of the present disclosure.

Referring now to FIG. 30, according to one embodiment the inserts 288 described above may also include patient specific contacting surfaces 294, for further matching the insert 288, in addition to the guide sleeves 254, with the patient specific anatomy. This allows greater stability and positioning of the insert 288, and the guide with the insert 288 included, in the proper location. In addition, for inserts 288 used in connection with a drill bit or other vibrating or oscillating tool, these patient matching surfaces 294 on the insert 288 would also prevent the distal end of the drill bit from "walking" or moving on the surface of the vertebral body when creating the initial pilot hole, thereby reducing the risk of incorrect trajectory of a fixation device.

According to further embodiments of the present disclosure, the patient contacting surfaces, formed by one or more protrusions extending from the main body of the surgical guide described in greater detail above (and according to several embodiments disclosed herein) may comprise a sharp or semi-sharp contacting edge for penetrating and affixing to the soft tissue surrounding the patient's anatomical feature, such as a facet joint. The contacting surfaces may, according to this embodiment, comprise recessed cavities for soft tissue incursion. These recessed cavities create edges around the outside of the legs, which could be sharp or selectively sharpened to facilitate cutting through soft tissue to rest/mate with underlying bone. This is particularly important for spinal surgical procedures where the precise location of the patient contacting surface must be within a small degree of error, and must remain permanent throughout the procedure.

Figure 31:
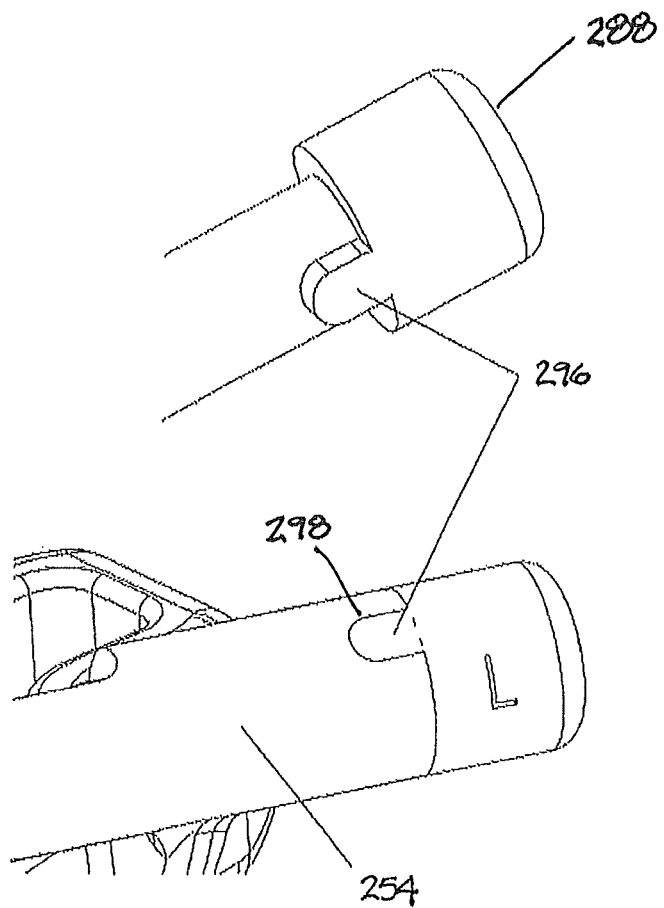
FIG. 31 is a perspective view according to yet another alternative embodiment of the present disclosure.
Figure 32A:
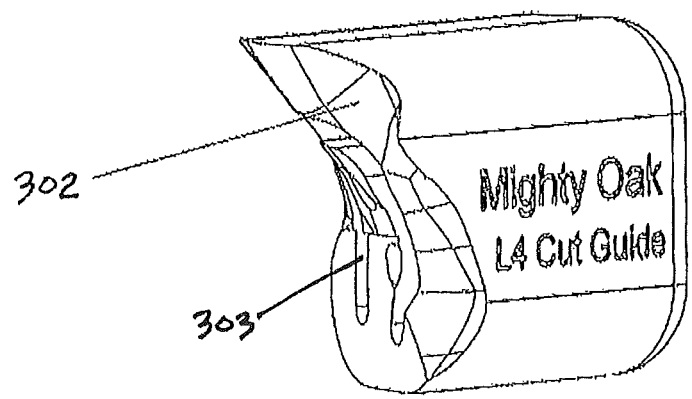
FIG. 32A is a perspective view according to yet another alternative embodiment of the present disclosure.
Figure 32B:
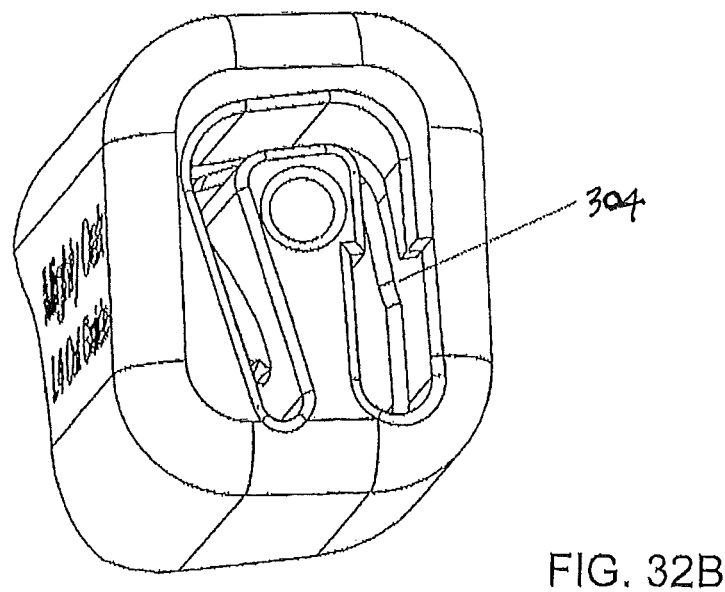
FIG. 32B is a perspective view according to the embodiment shown in FIG. 32A.

Referring now in detail to FIG. 31, the insert may further comprise a key or notch 296 about one surface of the body of the insert, which is configured to mate with a cutout or slot 298 on the guide sleeve 254 of the device. In this manner, the proper rotation/orientation of the insert 288 is insured when guiding the insert into the hollow body of the guide sleeve 254.

Referring now to FIGS. 32A-34B, further illustrations of a cutting guide (such as the one depicted in FIG. 13 above), are provided. According to one embodiment, the cutting guide comprises a plurality of patient specific contacting surfaces 302 about at least one surface of the cutting guide. The cutting guide further comprises, in a preferred embodiment, a patient specific "track" 303 for facilitating insertion of a cutting instrument (as shown in FIGS. 33A-C) and controlling the depth of insertion for that instrument to prevent unnecessary cutting of the underlying surface during a particular surgical procedure by further providing one or more instrument contacting surfaces 304. According to the embodiment shown in connection with FIGS. 32A-34B, the cutting guide may be provided for a laminectomy. According to other embodiments, the patient-specific guide may be fabricated for use in performing a corpectomy, a Pedicle Subtraction Osteotomy (PSO), a Smith-Peterson Osteotomy (SPO), a Vertebral Column Resection (VCR), or an Asymmetric Osteotomy (in either the sagittal or coronal plane), among others.

These patient-specific cutting guides may be fabricated from patient anatomical data, and may assist in performing complex procedures with greater certainty in their outcomes. For example, certain osteotomies, specifically PSO and SPO, require a great deal of surgical skill and are often time consuming. This is due in part to the intimate relationship of the vascular and neural elements to the boney structures, which create navigational challenges for a surgeon to safely and efficiently resect the bone during one of these procedures. This is especially true from a posterior approach. By using a patient-specific guide, a surgeon may confirm positioning and alignment of the cutting trajectory and path prior to initiating the procedure, and in furtherance of the disclosure provided above in relation to FIGS. 32A-34B, may also provide a degree of depth control essential for avoiding contact with vascular and neural elements.

In one embodiment, the cutting tool associated with the cutting guide shown in FIGS. 32A-34B is typical of the type of tools currently used in surgical procedures today. According to another embodiment, a specialty cutting bur or tip may be included with the instrument to facilitate further control of the location and depth of the instrument, as described in further detail below. For example, as shown in FIGS. 33A-33C, the cutting portion of the instrument may have a track ball 308 that prevents greater insertion of the instrument into the cutting guide than required for the patient specific procedure.

Figure 34A:
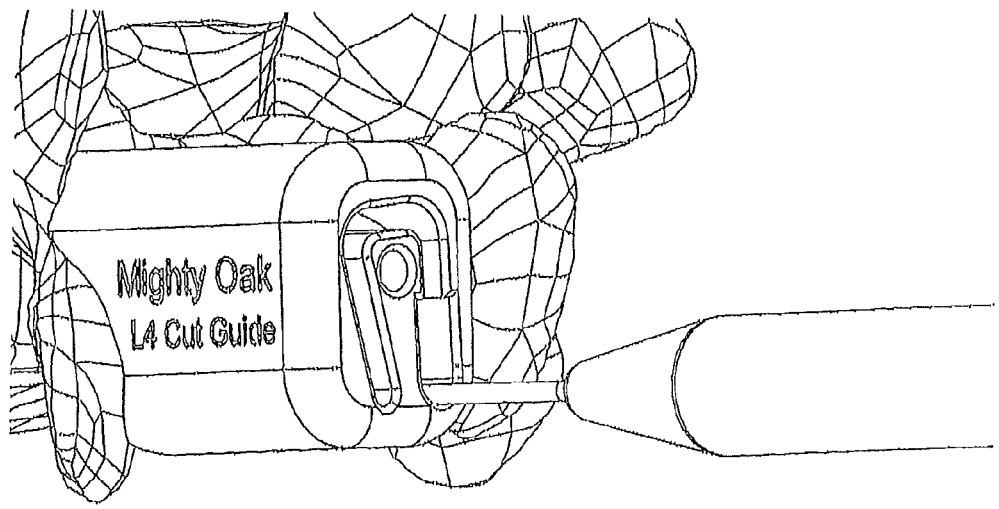
FIG. 34A is a perspective view according to yet another alternative embodiment of the present disclosure.
Figure 34B:
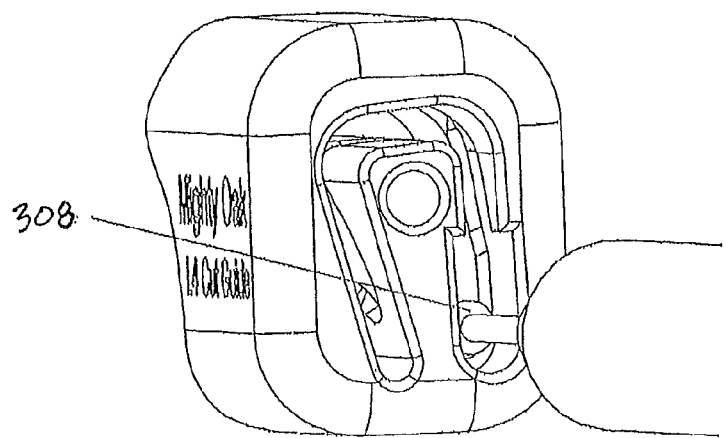
FIG. 34B is a perspective view according to yet another alternative embodiment of the present disclosure.

As shown in greater detail in FIGS. 34A-34B, the track ball 308 may be inserted into a first portion of the "track" 303 of the cutting guide, but not permitted to insert a second or deeper portion of the "track" of a cutting guide (through which the cutting surface is permitted to travel), thereby insuring proper depth of the cutting instrument. Further geometrical configurations other than those shown in FIGS. 34A-34B may be provided that allow the track ball 308 to move horizontally with respect to the top surface of the cutting guide, and in some instances laterally and downwardly into the track 303 of the cutting guide. In this embodiment, the cutting instrument would therefore be permitted to move at a certain depth about a patient's anatomy in a certain location of the "track" 303 of the cutting guide, but achieve a greater depth at yet other locations about the "track" 303 of the cutting guide. Thus, the depth permitted with respect to the instrument relative to the cutting guide may be variable about the "track" 303 of the cutting guide.

Other benefits achieved from the use of these patient-specific cutting guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Figure 35:
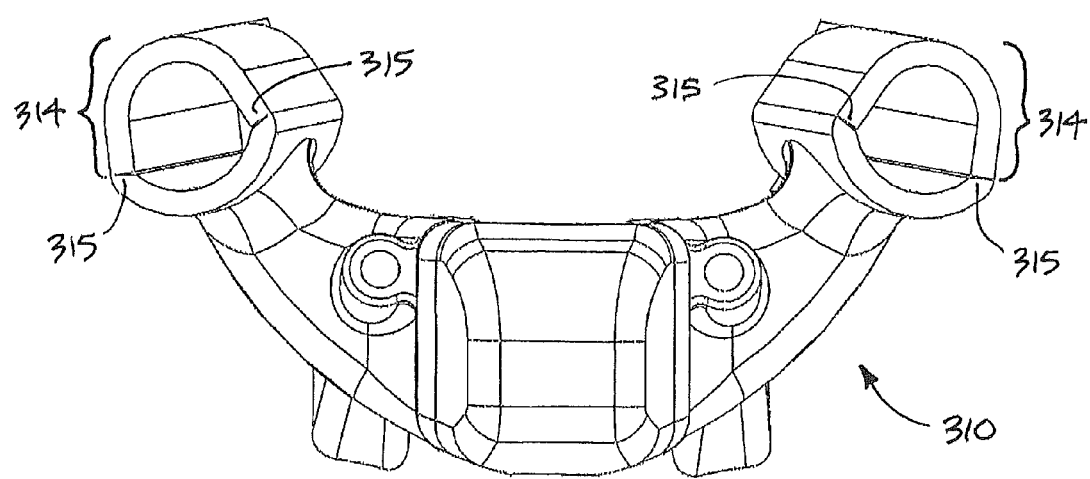
FIG. 35 is a top plan view according to yet another alternative embodiment of the present disclosure.

FIG. 35 is a top plan view according to yet another alternative embodiment of the present disclosure. In this embodiment, the device 310 may provide one or more patient contacting elements comprising break-away portions 314, which allow for placement of a fixation device (such as a pedicle screw) without detaching the device from the patient's boney anatomy. The break-away lateral edged may be formed by creating slots 315 in the surfaces of the surgical guide portions of the device, which provide perforation axes for the portions 314 to be broken.

According to this embodiment, the guide sleeve may be asymmetric, which would permit two different inner diameters: one that facilitates guidance of the hand tools (i.e. drill, tap) and one that accommodates the boss or cap of the device (such as the tulip of the pedicle screw). Once the break-away portion 314 of the guide sleeve is removed, a clear view and path to the vertebra is possible and allows pedicle screw placement without removing the guidance device.

Figure 36:
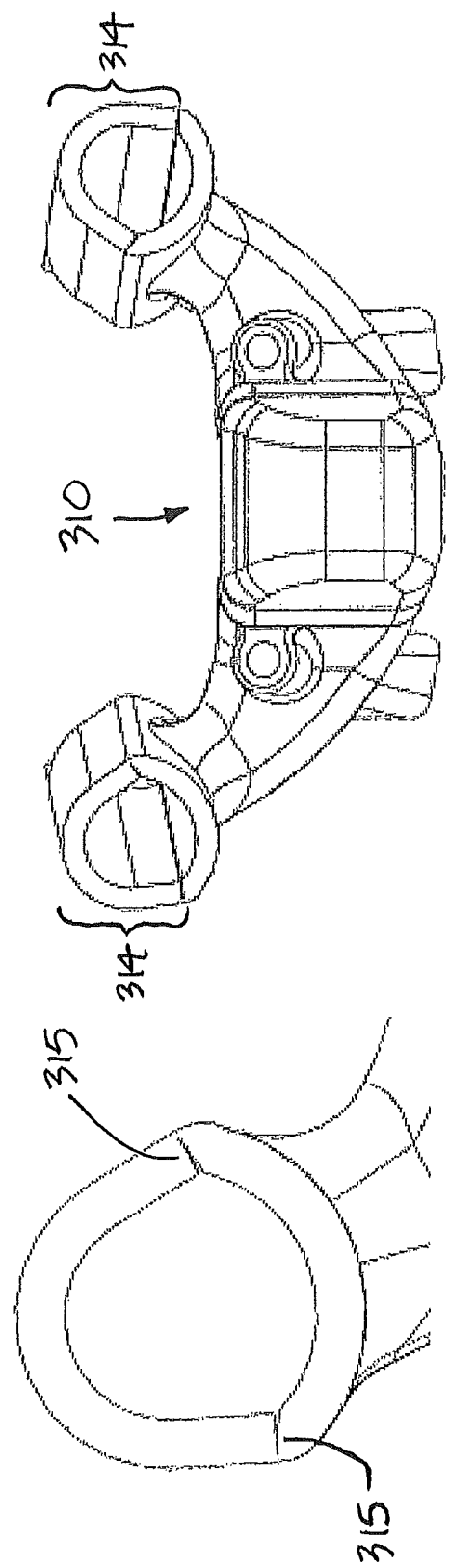
FIG. 36 is a detailed view of the device according to the embodiment shown in FIG. 35.

FIG. 36 is a detailed view of the device according to the embodiment shown in FIG. 35. In FIG. 36, a detailed view of the slots 315 are shown, which in a preferred embodiment may be formed during the fabrication of the device 310, but in alternate embodiments may be formed after the device has been fabricated by perforation or other techniques for creating a slot 315 about a certain surface of the guide sleeve of the device 310.

Figure 37:
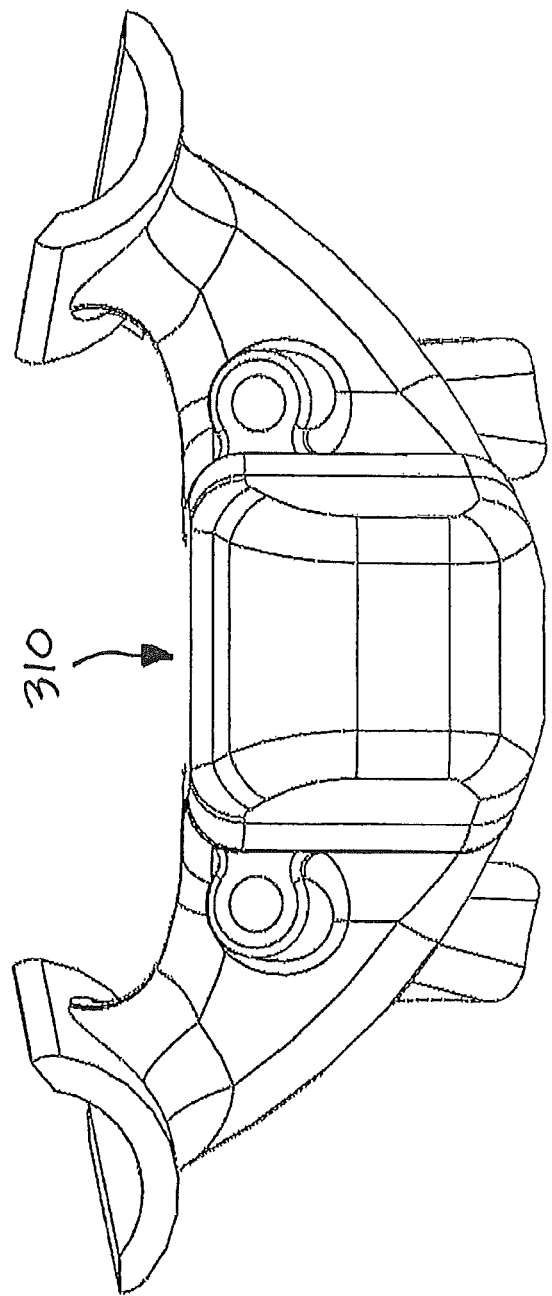
FIG. 37 is another top plan view of the device according to the embodiment shown in FIG. 35.
Figure 38:
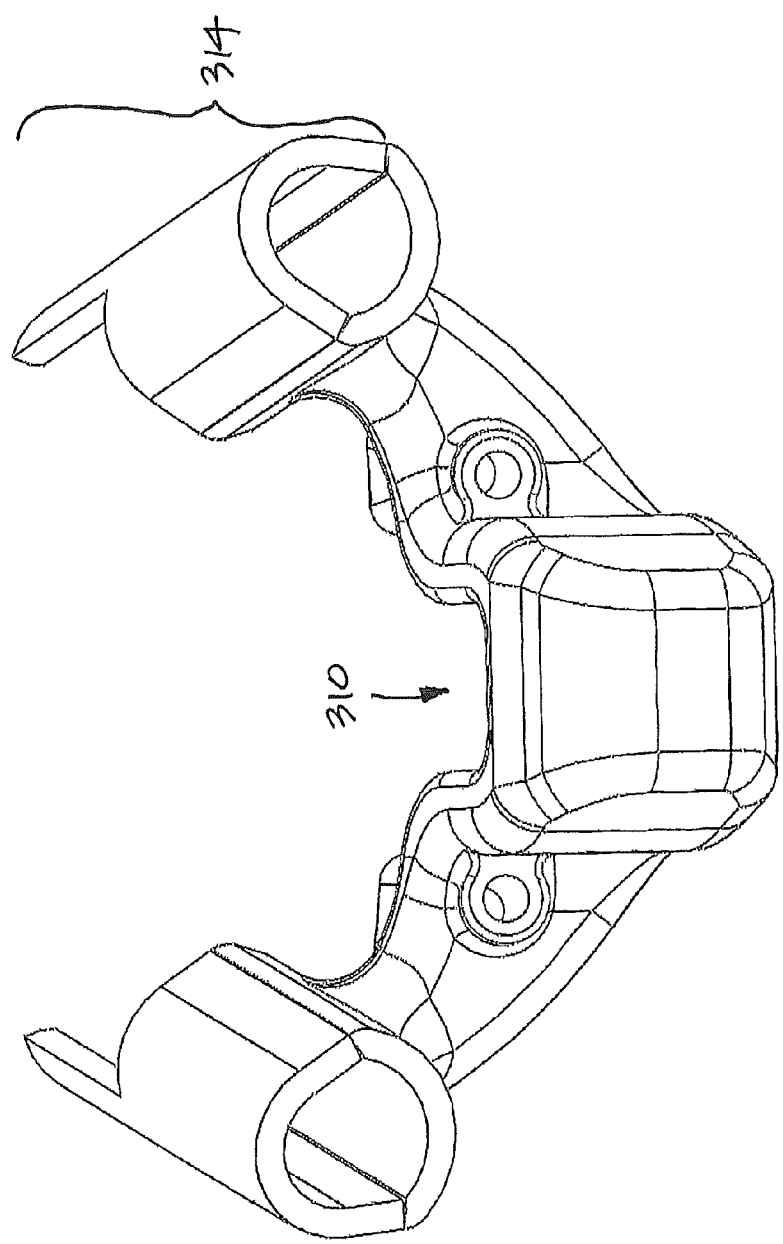
FIG. 38 is a top plan view according to yet another alternative embodiment of the present disclosure.
Figure 39:
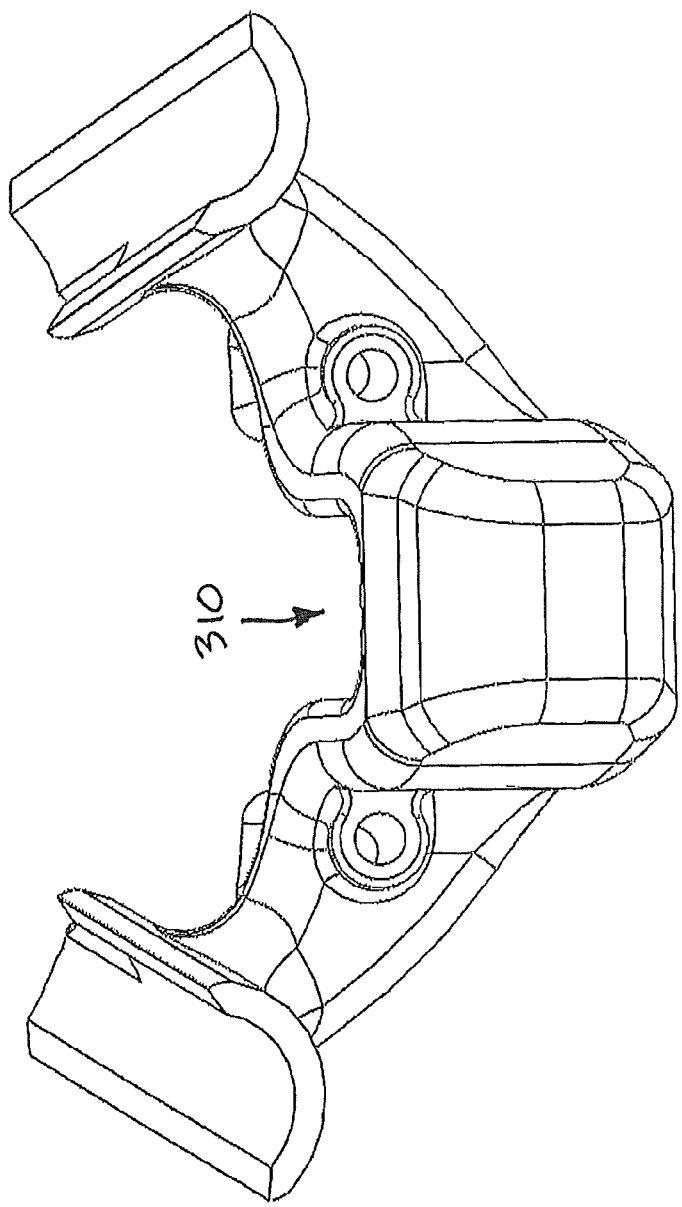
FIG. 39 is another top plan view of the device according to the embodiment shown in FIG. 38.

FIGS. 37-39 are additional views of the device according to the embodiment shown and described in relation to FIG. 35. In FIG. 37, the asymmetrical guide sleeve is shown with the two break-away portions 314 separated from the device 310. In FIG. 38, the embodiment shown and described in relation to FIGS. 26A-B is shown, but now having an asymmetrical guide sleeve with break-away portions 314 as described above.

FIGS. 40A-D are additional perspective views of the devices described above in relation to FIGS. 35-39, according to the embodiments having at least one or more break-away portions. Once removed, the break-away portions are preferably disposed by the surgeon.

Each of the embodiments described herein may be provided in a modular (i.e., single level) or a monolithic (i.e., multilevel) configuration. Thus, for ease of facilitating the description provided herein, certain embodiments have been shown in one (modular or monolithic) embodiment, but may be provided in a different (monolithic or modular) configuration without departing from the spirit of the disclosure. In various aspects, the monolithic embodiments may comprise anywhere from two to ten levels with respect to vertebral bodies, or enclose multiple locations of a patient's boney anatomy other than the spine. It is expressly understood that the embodiments described herein are for the purpose of illustrating certain embodiments of the disclosure, and are not intended to be limiting with respect to the scope of the disclosure.

The guide described herein preferably provides a surgeon with means to ensure proper location, trajectory, and depth of pilot holes through the underlying boney anatomy of a patient, such as for alignment and/or placement of fixation devices (i.e., screws). The guide may comprise a patient-contacting surface that is associated with an element of the guide other than the cannula(e). For example, the guide may comprise at least one footing or leg which comprises at least one patient-contacting surface. The patient specific surface can be specific to any portion of the patient's anatomy, as reflected in the captured patient data using any of the various methods described above.

The guide may further comprise a tab positioned on the opposite side of the guide from the patient-contacting surfaces. The tab may comprise a scoring, perforated surface or equivalent surface feature to improve purchase by a user's hand or fingers, and preferably provides a visible, manipulatable and ergonomic method for holding and directing the guide during use. The tab may also be used to translate forces from the user through the guide and into the patient contacting surfaces, including the clipping or hooking of the guide to anatomical features described below. Alternatively, the tab may comprise raised surface features, in lieu of scoring, and may further comprises extruded or shaped features to facilitate positioning and manipulation of the guide during a surgical procedure.

In embodiments, the cannulae are oriented and/or positioned in a specific location for placement of specific and/or patient-matched fixation or other devices. The cannulae of a particular guide may have different coloring, diameters, dimensions, heights, etc. to visually distinguish one from the other during surgery, and may comprise unique indicia to further aid in this distinction. The bores in the cannula may be depth specific to avoid under- of over-insertion of a particular device therethrough In embodiments, the patient-specific apparatus, as described herein, may be used in conjunction with particular robotic, navigational or motion control systems, including systems pertaining to fixation-related surgeries. More specifically, these guides may be used in conjunction with devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The patient-specific apparatus, as described herein, may be used in conjunction with particular robotic, navigational, motion control or AR systems, including systems pertaining to fixation-related surgeries. For example, the apparatus described herein may be used in conjunction with an AR system for assisting with placement and orientation of a guide, including but not limited to the patient-matched guide described herein, during a particular surgical procedure.

The AR system may be employed with a physical guide adapted to be placed in at least one of the contact locations displayed by the AR system. One advantage to having a physical guide for use in conjunction with the AR system is that the physical guide may work regardless of movement between individual anatomical features, whereas use of a purely "virtual" system alone may not be accurate, particularly when there is movement following initial registration. Physical guides used in a surgical procedure will still have an image generated from patient-imaging data captured during the surgery and may be loaded into the AR's software or other configuration program for viewing by the surgeon.

The AR system of this embodiment may be utilized in conjunction with the one or more patient-specific guides to ensure proper alignment of the guides with the patient's anatomy, where contact locations of the guide will display on the actual boney anatomy so the surgeon can align the guide with the contact locations. Knowing the correct guide placement (of the physical guide) helps ensure adequate cleaning of soft tissue around the contact locations.

In addition, one or more trajectories may be displayed by way of the AR system, including through an associated peripheral imaging device, including those described below. These trajectories may be displayed with different indicia, colors, shapes or styles to indicate points of distinction from one trajectory and another trajectory, or alternatively the order or sequence of the trajectories. In this manner, the surgeon may utilize the one or more trajectories for guiding, for example, an instrument or an implant to the precise location shown by the imaging device.

The AR system may further comprise a peripheral imaging device, such as a headset or other wearable device, to permit the surgeon or other health professional view the images displayed by, for example, an associated AR program. Additional devices, such as handheld devices, voice activated devices, headphones, speakers, microphones, haptic devices and controls, holographic imaging equipment, visual displays (including without limitation on-glass display technologies such as Google Glass), and other components provided with AR systems may be supplied to facilitate the objectives described above. In this regard, U.S. Patent Publication Nos. 2020/0092462, 2020/0089314 and 2020/0082621, as well as Applicant's U.S. Pat. No. 10,580,268 are hereby incorporated by reference in their entireties for the purpose of supplementing this disclosure, pursuant to 35 U.S.C. § 112.

In embodiments, the AR system may also display pre-surgically or post-surgically planned trajectories and/or cutting planes so that a surgeon can align actual instrumentation with the planned procedure, whether that procedure includes insertion of an instrument or implant or a cutting or removal operation. These trajectories of insertion or path of cuts may be virtually projected (similar to the projection of locations on the patient's boney anatomy referred to in FIGS. 15-16) in a plane extending away from the patient's boney anatomy so that a surgeon can clearly see the intended path or placement of instrumentation. In this embodiment, the use and placement of a physical guide (and its associated mechanical constraints) helps to ensure proper pathway is followed.

In embodiments, the AR system described herein may facilitate placement of instruments or implantable devices. The system may be employed to ensure proper placement of plates, plates and rods, or rods alone, including the proper arcuate shape and any necessary bending of the rods used in a particular surgical procedure. The system may be used both pre-surgically and during the surgical procedure, as new registration and/or visualization data is captured by the system. For example, the system may be used for visualizing and executing planned osteotomy cuts or drilling of holes in the patient's boney anatomy, wherein the display of the system shows what areas and/or segments of bone need to be removed to make pre-surgically planned correction. As another example, the system may be used to show and facilitate execution of planned sagittal alignment (to aid in rod bending), or to show planned bone correction to help surgeon achieve desired amount. This example may be used to facilitate procedures on the patient's cervical spine as well.

The AR system described herein may also be configured to indicate where areas of critical anatomy are located (e.g. abdominal aorta, spinal cord, existing nerve roots), including those areas that are sought to be avoided. In this manner, the surgeon may be notified when an instrument or implant (or other device) is approaching a sensitive area to prevent injury. For example, when drilling a pilot hole, the AR system may be configured to compare the planned trajectory with the actual trajectory during the course of the surgical procedure and alert the surgeon that the trajectory deviates (e.g., becomes too medial/inferior/lateral/superior) from the planned trajectory. The use of alerts in this manner may also apply to desired cuts, instrument depth, etc. so that if the course of the surgical procedure does not closely match the planned procedure, the system will provide an alert and recommended correction. In certain embodiments, this deviation may be preset by the surgeon (e.g., by 5-8% or by a preset distance).

In still other embodiments, the system is configured to automatically send alerts when the actual procedure approaches one of the sensitive landmarks or deviates from the planned procedure. In still other embodiments, the system may display locations to avoid during the surgical procedure, such as a defined negative space relative to the targeted surgical site, or alternatively display radiation safe zones in a surgical suite or operating room, for example in relation to a C-arm. The system may also be configured to display sterile environments/instrumentation and send alerts if there is a change in state during a procedure. For example, if something is dropped or comes into contact with a non-sterile environment, the system could automatically change its display state to "non-sterile" or provide an equivalent alert.

In embodiments, a screw and/or instrument may also be subject to alerts, and the location of each determined by the AR system during use. In this manner, the system ensures the implanted screw or instrument is advanced in a correct trajectory and depth. The advancement and location of the screw or instrument may be displayed to the surgeon or other user via a wearable device, by way of example, and thereby provide the user with confirmation that the instrument and screw was placed correctly. In this manner, a surgeon may attach a patient-specific apparatus to multiple levels of the patient's spine that is impacted by a particular surgical procedure, and thereby provide markers for registration and orientation without having to rescan the patient throughout the surgery. In turn, the robotically guided surgical device may view the patient through the markers and align instrumentation controlled by the robotic equipment. This alignment may be achieved by any one of a combination of guides/markers/patient-specific orientation guides described herein.

Furthermore, the guides described herein may be provided with embedded locating/information markers. Thus, the robotic device(s) may orient robotically controlled instruments relative to a drill location and embedded information on each level a guide is present. In certain embodiments, such as with a prior fusion procedure, only one guide/locating marker would be needed. In some embodiments, the apparatus is 3D printed with metal or plastic material. In other embodiments, the apparatus is fabricated using one of the other methods described herein.

Autonomous and semi-autonomous systems may further comprise an adjustable, robotic arm assembly, which may be affixed to a piece of machinery, an operating surface or alternatively to the patient. The arm assembly may substantially facilitate the placement of surgical screws during spinal surgeries by securing the guide and corresponding coupling devices to a stationary surface, thereby providing greater stability and, in turn, more accurate placement of screws and/or other fixation devices. For example, a patient specific guide may be engaged with the corresponding patient specific anatomy of a desired surgical site. An adjustable arm assembly, which is secured to a stationary surface, such as an operating or side table or other surface, can then engage the guide via corresponding coupling devices to provide greater stability and delivery of fixation devices therethrough. This attachment between the device(s) and the arm assembly may permit a user to set and fix, for example, the sagittal angle of the device(s) when performing a surgical procedure on the patient's spine.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

In one embodiment, the guides described herein are designed following acquisition of a scan of the patient's anatomy with a medical imaging device. The scan may be performed by a CT scanner, an MRI scanner, or any other medical imaging device. The scan is segmented into 3D models of each vertebra. These 3D models are then modified in CAD to simulate the correction desired by the surgeon. Once the desired correction is appropriately simulated, a guide is generated that will allow the surgeon to make the planned corrections intraoperatively. The guides may then be manufactured through 3D printing, rapid prototyping, or an alternative method for creating patient-specific features.

The guides of the present disclosure can be used as physical cutting guides, drill guides, bone removal guides, implant guides, screw guides, instrument guides or guides for other surgical equipment or instrumentation. Additionally, the guides may be used as an aid to indicate to surgeons the angle and location of drilling or cuts so that neural elements in the patient's spine or vertebral arteries are not harmed. The guides may also be used pre-surgically on models of the patient's anatomy to test or practice the planned surgical procedure. At least a portion of the proximal end of the guide is configured to extend outside of the patient during a surgical procedure.

In one embodiment, at least a portion the guide is reusable. Optionally, at least a portion of the guides projects beyond the patient's anatomy when in a position of use during a surgical procedure. For example, at least a proximal portion of a cannulae of one or more of the guides may project from an incision formed during surgery.

Additionally, the patient-specific guides may comprise individual pieces that are adapted to be assembled by a surgeon before, or during, a surgical procedure. The portions or components of the guides may be disassembled and delivered to a specific area of the patient's anatomy for assembly during the surgical procedure. For example, the bodies, cannulae, and legs of the guides may pass through a bore of a cannula of another tool and assembled during a minimally invasive surgical procedure.

The cannula described herein may be configured to contact, by way of example but not limitation, one or more of the lamina, pars interarticularis, aspects of the transverse process, the inferior articular process, the spinous process and the superior articular process of the patient. Cutouts (not illustrated) may be formed on a portion of the cannulae to prevent the guide from contacting the spinous process of the patient, adjacent vertebrae, or to avoid other patient anatomy.

The cannulae may have a generally cylindrical or oval shape but other shapes are contemplated. Each one of a pair of cannulae may have a unique orientation and size. The cannulae may be of any length and differ from one cannula to another cannula provided with the apparatus, based at least in part on the specific patient's anatomical features, preferences of the surgeon, orientation of the guide, and the type of tool or fixation device associated with the cannulae. The length of the cannulae may also be selected to provide depth control of instruments guided by the cannulae. For example, in one embodiment, the cannulae has a first length to allow a drill bit to penetrate a first depth into the patient's anatomy. In another example, the cannulae has a second length that is greater than the first length. Accordingly, the cannulae prevents the drill bit from penetrating the first depth into the patient's anatomy.

The cannulae may optionally include extensions of any size or shape. In one embodiment, the extensions are positioned proximate to a distal end of the cannulae. In another embodiment, the extensions wrap at least partially around the exterior of the cannulae. The extensions may also project at least partially beyond the distal end of the cannulae. The extensions are adapted to wrap at least partially around a predetermined portion of the patient's anatomy. In one embodiment, the extensions are adapted to wrap around a portion of one of the pars and the superior articular process.

In one embodiment of the present disclosure, the bore of the cannulae may facilitate and guide a drill bit, or any other suitable instrument to drill and tap a pilot hole in any one or more of the trajectories described herein. After the pilot hole is created, the bore may further guide insertion of a fixation device into the pilot hole. In another embodiment of the present disclosure, the bore may be adapted to receive one or more inserts or guide wires.

Various benefits achieved from the use of these patient-specific guides include: providing means to achieve quick and controlled removal of bone; providing spatial orientation of cutting tools used during the procedure; ensuring correct orientation, both through controlled guiding of the instrument and visualization during the pre-surgical planning process; providing accurate calculation of deformity correction, prior to operating; providing accurate bone resection, which in turn ensures deformity correction; depth controlled or hard stop restrictions to protect neural and vascular elements; controlled cutting or insertional vectors and avoiding contact or injury to neural elements; and ability to provide approach for cuts or implantation in a posterior, anterior, posterior lateral, transforaminal or direct lateral approach.

Additionally, the guides described herein facilitate quicker bone removal and instrumentation of the patient's boney anatomy, decreasing surgical time and associated risk to the patient. These guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

Although embodiments are described and in certain figures shown as one piece, it will be appreciated that in other embodiments the guide could include multiple pieces or a series of guides that are placed in a specific order to generate a series of operations or actions. In embodiments of guides comprising multiple pieces, each piece of the guide may be keyed to interconnect in a specific order and location to other pieces of the guide. In one embodiment, the guide does not contact the patient's anatomy. In another embodiment, at least a portion of the guide is adapted to contact the patient's anatomy.

Although the devices described above have been illustrated for use with certain guide screws and/or instruments, it is expressly understood that the devices may be used with a variety of other implantable and non-implantable apparatus, including by way of example, lateral mass screws. Other screws and instruments may be used with the surgical devices described above without departing from the spirit of the disclosure and are considered to be within the scope of the appended claims.

The apparatus described herein may facilitate the introduction of Kirschner wire (K-wire) that may be visualized through various imaging systems known in the art, and which may further be used to identify a desired patient-specific marker or location. Such procedure may also allow for successful dilation through the introduction of sequential muscle or soft tissue dilators, which may allow for a quicker, more effective operation. The use of such apparatus, as discussed above, may also prevent the need of additional surgical devices, such as multiple retractors of various sizes, which may substantially reduce the logistics and cost of preparation of an operation.

Other embodiments of the present disclosure may include patient specific insertional guides that may include patient-specific contours or channels that conform to anatomical markers. Such patient specific insertional guides may be used for the placement of external hardware or guide surgical equipment or instrumentation for percutaneous and/or subcutaneous introduction, which may be predetermined using medical imaging and/or computer aided design software as described in conjunction with the systems and methods disclosed herein. In such procedures, the external hardware and/or surgical equipment may be guided via the patient-specific contours or channels by location, axes and/or insertional trajectories, and/or depth to substantially ensure accuracy. In these embodiments, hardware or instrumentation is substantially guided during surgery via predetermined patient-specific anatomical markers on a surgical area of interest. Said another way, at the time of surgery the guide may be placed at a predetermined surgical location, either percutaneously or subcutaneously, that can then direct and facilitate the operation by way of accurate introduction of external hardware or guided surgical equipment or instrumentation. Such procedures may also substantially guarantee the safety and reliability of the procedure.

The models, templates and other patient-specific or patient-matched apparatus described herein may be manufactured by any known method of manufacture, or by methods developed after the date of this disclosure. In one embodiment, models are manufactured using a rapid manufacturing process such as 3D printing, although other processes are contemplated. The models can be fit to the patient's anatomy during surgery to help the surgeon visualize the correct angles and starting locations for cuts, inserting drills or other surgical instruments, or introducing an implant, such as a plate or screw. In one embodiment, the models include at least one cannula. The cannula(e) may be adapted to receive fixtures to at least temporarily interconnect the model to portions of the patient's anatomy. Fixtures may also be received in the cannula to interconnect portions of a modular model together.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

Other benefits achieved from the use of these patient-specific guides of all embodiments of the present disclosure include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

Additionally, the guides facility quicker bone removal and instrumentation of the patient's boney anatomy, decreasing surgical time and associated risk to the patient. The guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, ployamide, resins, particularly fiber-encased resinous materials rubber, nylon, latex, synthetic rubber, synthetic materials, polymers, and natural materials.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the use of various technologies for capturing a patient's unique morphology, and subsequently mapping and/or planning the fabrication of a device comprising one or more "patient matched" surfaces or features for complementing that unique morphology. Further, such devices may be further optimized with respect to the unique data associated with the patient, such that the device may be matched with specific devices for use during the surgical procedure, or oriented around the patient's own anatomy to achieve, for example, one or more desired insertional trajectories (which may be verified in a pre-operative setting). Variations on this step, and the inclusion or exclusion of additional steps described herein are expressly contemplated by the present disclosure.

According to various embodiments described herein, the patient-matched apparatus may further comprise desired axes and/or insertional trajectories. According to embodiments, the patient-matched apparatus may be further matched with at least other apparatus used during the surgical procedure. The apparatus may be configured to receive markers or may include markers embedded within the guide, the position of which (relative to the patient-contacting and other elements/components of the guide) are easily registered and determined by the autonomous or augmented equipment employed during the procedure. Other features of the disclosure will become apparent after a review of the following disclosures and varying embodiments of the disclosure.

The guide preferably provides a surgeon with means to ensure proper location, trajectory, and depth of pilot holes through bone, such as for alignment and/or placement of a plate and associated fixation devices (i.e., screws). The patient specific surface can be specific to any portion of the patient's anatomy, as reflected in the captured patient data using any of the various methods described above in the Summary.

The guide according to one embodiment may comprise one or more extensions. Extensions may be sized such that the body of the guide is appropriately located in the proper location. In one embodiment, one or more extensions may be sized, shaped or otherwise adapted to at least partially hook around a portion of the patient's anatomy to ensure proper placement and avoid movement of the guide. For example, the distal ends of the one or more extensions may comprise shaped "hooks" that at least partially wrap around and latch onto complementary surfaces of the specific patient. In certain embodiments, the extensions or portions thereof may be at least semi-malleable so that the extensions may deflect slightly and snap into place once engaged with the patient's boney anatomy. In other embodiments, the curvature or "hooks" of the extensions may comprise compound curvatures, or otherwise have curves in at least two different planes formed by two distinct portions of the patient's anatomy.

The guide may contain additional extensions or connectors, which in certain embodiments are removeable from the body of the guide, and which may contact the C1 vertebra (or any other cervical level) to ensure proper orientation and/or stability of the guide. In the version of the guide where a portion is implantable, the implantable portion may extend to C 1 or C2 and provide trajectories for placing screws in those levels of the vertebrae as well. In this scenario, this device is acting not only as a guide, but also aligns anatomy with a specific amount of correction and maintains that correction, similar to a rod/screw construct. In other embodiments, the guide may comprise a connector between C1 and C2, such that the guide and connector(s) span from Oct. to C2.

The guide may not include a large patient-specific surface as described above. Instead, the guide may be held in place by fixation pins, suction, or by manual pressure applied to the body of the guide. The guide may contain additional feature(s) that act as a "pressure plate" where the user applies force to hold the guide in position. In certain embodiments, the pressure plate(s) are patient-specific. In other embodiments, the pressure plate(s) are not patient-specific.

The guide may comprise an additional feature or surface oriented to identify, separate and/or protect critical anatomy such as the venous sinus. In one embodiment, the feature is comprised of a substantially planar surface of the guide that acts a shield to soft or sensitive tissue. In other embodiments, the surface comprises an arcuate or curved surface to better distract the surrounding tissue while avoiding damage to the same. In embodiments, the shielding surface of the guide may be removable or adjustable to account for specific tissue the surgeon or health professional preferences.

Although not illustrated in the appended drawing figures, the guide may further comprise attachment points formed in one or more of the body, the cannulae, and the legs. The attachment points are adapted to receive one or more secondary or tertiary cannulae. The cannulae may include a bore or a cutting slot to guide an instrument to target another portion of the patient's anatomy. In one embodiment, the cannulae are adapted to target one or more predetermined portions of the cervical spine (i.e., C1-S1 and ilium).

In one embodiment, the attachment points comprise slots to receive extensions of the cannulae. In one embodiment, the slots may also direct the path of a blade or other cutting instrument, or to receive a measurement aid or tool for facilitating the surgeon/user in identifying landmarks, surrounding boney anatomy, placement of implanted devices, or for surgical planning.

The guide may also include indicia to identify a sequence of use or portions of the patient's anatomy with which the guide is to be used. The indicia may also indicate a tool to be used, a direction of a cut to be performed, or a planned orientation or alignment of the guide. According to one embodiment, the guide may further comprise one or more indicia for identifying the guide with a particular patient.

The patient specific surfaces may include any number of protrusions, depressions, and contours to substantially conform to the patient's anatomy. For example, the patient specific surfaces may comprise multiple portions that are adapted to contact two different planes formed by two distinct portions of the patient's anatomy. The patient specific surfaces are adapted to one or more of: align the insert in a predetermined position with respect to the patient's anatomy; hook around a portion of the patient's anatomy; prevent unintended or inadvertent movement of the insert during a surgical procedure; and displace soft tissue. In one embodiment, the patient specific surfaces comprise relatively thin extensions to displace soft tissue. By protruding at least partially around and substantially conforming to different portions of the patient's anatomy, the patient specific surfaces generally "hook" at least partially around (or to) the patient's anatomy. Thus, the surfaces may contact at least two different planes formed by distinct surfaces of the patient's anatomy. Accordingly, the insert is adapted to at least partially fit and substantially conform to predetermined portions of one or more vertebrae during the surgical procedure.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

Additionally, although the fusion cages of the present disclosure are particularly well-suited for implantation into the spinal column between two target vertebrae, and although much of the discussion of the present disclosure is directed toward their use in spinal applications, advantages offered by embodiments of the present disclosure may also be realized by implantation at other locations within a patient where the fusion of two or more bony structures may be desired. As one of skill in the art will appreciate, the present disclosure has applications in the general field of skeletal repair and treatment, with particular application to the treatment of spinal injuries and diseases. It should be appreciated, however that the principles of the present disclosure can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A patient-specific guide that mates with anatomical features of a particular vertebra, comprising:
    a body;
    a first wing extending from the body and coupled to a first column, wherein the first column comprises a lower surface that anatomically mates with at least one first contour of the particular vertebra; and
    a second wing extending from the body and coupled to a second column, wherein the second column comprises a lower surface that anatomically mates with at least one second contour of the particular vertebra;
    wherein the lower surfaces of the first and second columns are determined from and complementary to a patient's anatomical data.

2. The guide of claim 1 further comprising at least one predetermined trajectory, wherein the at least one predetermined trajectory is selected from a list comprising a pedicle screw trajectory, a cortical bone trajectory, a cortical trajectory, a sacral pedicle trajectory, a sacral alar trajectory, an S2-alar-iliac trajectory, an iliac trajectory, a transarticular trajectory, a lateral mass trajectory, a translaminar trajectory, a transcondylar trajectory, a cervical pedicle screw trajectory, a sub axial lateral mass screw trajectory, a transpedicular screw trajectory, a pars screw trajectory, an occipitocervical screw trajectory, an occipital screw trajectory and an occipital condyle C1 screw trajectory.

3. The guide of claim 1 further comprising an extension, the extension comprising a distinct patient-specific surface configured to mate with a third contour of the particular vertebra.

4. The guide of claim 1, wherein proximal ends of the first and second columns are a pre-determined distance from a respective predetermined portion of the anatomical features.

5. The guide of claim 4, wherein proximal ends of the first and second columns provide a fixed reference point for depth control of instrumentation passing through the first and second columns.

6. The guide of claim 1, wherein lower surfaces of the first and second column comprise a surface feature configured to clip on, under or around a portion of the anatomical features.

7. The guide of claim 6, wherein the portion of the anatomical features comprises one or more of a posterior tubercle, posterior arch, posterior lateral mass, superior articular process, inferior articular process, pars, lamina, spinous process and transverse process.

8. The guide of claim 1, further comprising a tab positioned on the body for holding and directing the patient-specific guide during use.

9. The guide of claim 8, wherein the tab comprises extruded features to facilitate positioning and manipulation of the patient-specific guide.

10. A patient-specific guide, comprising:
    a body;
    a first column oriented in a predetermined trajectory;
    wherein at least a portion of the first column comprises a plurality of patient-specific contours derived from patient-specific data obtained from a patient and configured to mate with one or more patient-specific features; and
    wherein the predetermined trajectory of the first column is determined at least in part from bone density data obtained from the patient.

11. The guide of claim 10 further comprising a second column oriented in a predetermined trajectory determined at least in part from bone density data obtained from the patient.

12. The patient-specific guide of claim 11, wherein the one or more patient-specific features are associated with a patient's vertebrae.

13. A patient-specific guide for use in a spine-related surgery on a patient, comprising:
    a holding tab extending from one end of the guide;
    a first and second column oriented in a predetermined trajectory;
    at least a first projection on a distal end of a first cannula;
    at least a second projection on a distal end of a second cannula;
    wherein distal ends of the at least a first and second projection comprise distinct patient-specific surfaces configured to mate with anatomical features of the patient; and
    wherein the first and second column further comprise a first and second bore configured to receive a tool or instrument to create an aperture in the anatomical features of the patient.

14. The guide of claim 13 further comprising at least one predetermined trajectory, wherein the at least one predetermined trajectory is selected from a list comprising a pedicle screw trajectory, a cortical bone trajectory, a cortical trajectory, a sacral pedicle trajectory, a sacral alar trajectory, an S2-alar-iliac trajectory, an iliac trajectory, a transarticular trajectory, a lateral mass trajectory, a translaminar trajectory, a transcondylar trajectory, a cervical pedicle screw trajectory, a sub axial lateral mass screw trajectory, a transpedicular screw trajectory, a pars screw trajectory, an occipitocervical screw trajectory, an occipital screw trajectory and an occipital condyle C1 screw trajectory.

15. The guide of claim 13, wherein the tool or instrument is selected from a list comprising a drill bit, a high-speed bur, a wire, a k-wire and a tap.

* * * * *